(12) United States Patent
Cowart et al.

(10) Patent No.: US 11,911,317 B2
(45) Date of Patent: Feb. 27, 2024

(54) STACKABLE EYE SHIELDS WITH SELECTIVELY RELEASABLE SNAP-FIT ASSEMBLY

(71) Applicant: DeRoyal Industries, Inc., Powell, TN (US)

(72) Inventors: Walter C. Cowart, Blaine, TN (US); Ethan Edward Valentine, Knoxville, TN (US); Nicholas John Poker, Knoxville, TN (US); Phillip David Peery, Sweetwater, TN (US)

(73) Assignee: DeRoyal Industries, Inc., Powell, TN (US)

( * ) Notice: Subject to any disclaimer, the term of this patent is extended or adjusted under 35 U.S.C. 154(b) by 200 days.

(21) Appl. No.: 17/477,697

(22) Filed: Sep. 17, 2021

(65) Prior Publication Data
US 2022/0133541 A1     May 5, 2022

Related U.S. Application Data

(63) Continuation-in-part of application No. 17/218,610, filed on Mar. 31, 2021.
(Continued)

(51) Int. Cl.
*A61F 9/02*     (2006.01)

(52) U.S. Cl.
CPC .................. *A61F 9/025* (2013.01)

(58) Field of Classification Search
CPC .......... A61F 9/025; A61F 9/027; A61F 9/028; A61F 9/02; A61F 2009/021
See application file for complete search history.

(56) References Cited

U.S. PATENT DOCUMENTS

| | | | |
|---|---|---|---|
| 653,086 A | 7/1900 | Houts | |
| 1,380,561 A | 6/1921 | Kaufmann | |

(Continued)

FOREIGN PATENT DOCUMENTS

| | | | | |
|---|---|---|---|---|
| EP | 2305190 A1 | * | 4/2011 | ............ A61F 9/025 |
| GB | 1210962 A | | 11/1970 | |
| GB | 2442755 A | | 4/2008 | |

OTHER PUBLICATIONS

International Searching Authority, Kari Rodriquez, Notification of Transmittal of the International Search Report and the Written Opinion of the International Searching Authority, or the Declaration, dated Jan. 11, 2022.

*Primary Examiner* — Marin Pichler
*Assistant Examiner* — Justin W. Hustoft
(74) *Attorney, Agent, or Firm* — Luedeka Neely, P.C.

(57) ABSTRACT

A stack of eye shields includes a plurality of eye shields each having a frame with receivers located along the frame and latches located to engage the receivers, and spaced apart elevated support surfaces along and rising above an upper portion of the frame; and a lens installed on the frame and having lens apertures extending through the lens and aligned with the receivers of the frame, with the latches engaged with the receivers securing the lens to the frame. The eye shields are stacked one on top of another with each of the eye shields oriented substantially parallel to one another with each of the elevated surfaces of an overlying one of the frames of the stack being slightly forward of a corresponding one of the elevated surfaces of the underlying frame of the stack, with each frame of each eye shield of the stack having a gap therebetween except at contact surfaces where the elevated support surfaces contact an adjacent lower surface of an overlying eye shield. The elevated support (Continued)

surfaces of the frames stabilize the stack of the eye shields for shipping and dispensing of the stack of the eye shields.

9 Claims, 22 Drawing Sheets

Related U.S. Application Data

(60) Provisional application No. 63/109,034, filed on Nov. 3, 2020, provisional application No. 63/089,897, filed on Oct. 9, 2020.

(56) References Cited

U.S. PATENT DOCUMENTS

| | | |
|---|---|---|
| 1,860,324 A | 5/1932 | Einson |
| 2,006,445 A | 7/1935 | Davidson |
| 2,030,996 A | 2/1936 | Lustig |
| 2,031,575 A | 2/1936 | Roe |
| 2,137,906 A | 11/1938 | Cummings |
| 2,517,030 A | 8/1950 | Ringler |
| 4,822,158 A | 4/1989 | Porsche |
| 5,375,702 A | 12/1994 | Fiallo |
| 6,533,412 B1 | 3/2003 | Wang et al. |
| 6,964,067 B1 | 11/2005 | Hartman |
| 7,096,513 B1 * | 8/2006 | Kress ............... A42B 3/328 2/425 |
| 7,661,815 B2 | 2/2010 | Lipawsky |
| 8,992,007 B2 | 3/2015 | Li |
| 10,517,763 B2 | 12/2019 | Quinn et al. |
| 10,543,955 B1 | 1/2020 | Turturro et al. |
| 10,702,345 B2 | 7/2020 | Saito et al. |
| 2003/0019005 A1 * | 1/2003 | Burnett ............... A61F 9/02 2/10 |
| 2008/0087556 A1 | 4/2008 | Henke et al. |
| 2009/0188015 A1 | 7/2009 | Grad et al. |
| 2009/0314661 A1 | 12/2009 | Fisher et al. |
| 2017/0239089 A1 * | 8/2017 | Quinn ............... A61F 9/025 |
| 2018/0228652 A1 * | 8/2018 | Ohura ............... A61F 9/027 |

* cited by examiner

STACKABLE EYE SHIELDS WITH SELECTIVELY RELEASABLE SNAP-FIT ASSEMBLY

FIELD

The present disclosure relates to eye shields. More particularly, the disclosure relates to improved molded eye shield structures configured to be stackable and having an improved selectively releasable snap-fit latch that provides improved function for ease of assembly and disassembly, stacking of the eye shields, and improved aesthetics.

BACKGROUND

Improvement is desired in the manufacture of disposable eye shields of the type having a molded plastic frame with ear pieces and a lens that is secured to the frame to provide an eye shield.

One need in the prior art is for eye shields that can easily be stacked one on top of another for shipping and dispensing and that tend to remain parallel to one another in the stacked orientation. Conventional eye shields are provided in stacks in boxes, but the eye shields become entangled and shifted and become difficult to dispense without a user handling several of the eye shields at a time.

The present disclosure advantageously provides aesthetically pleasing eye shields configured to facilitate stacking of the eye shields so that the eye shields remain aligned and parallel to one another and do not entangle so that a user can just grasp the top most eye shield from the stack and not have to handle underlying ones.

The present disclosure also advantageously provides eye shields having a snap-fit feature that enables the lens to be easily attached to the frame and also to be easily removed for cleaning or replacement. The snap-fit feature is also specially configured to facilitate stacking of the eye shields.

Also provided in the disclosure is a container that aesthetically and structurally compliments the stacked eye shields and facilitates shipping and dispensing of the eye shields.

SUMMARY

The above and other needs are met by an improved eye shield configured to be provided in a stack of like eye shields for shipping and dispensing.

In one aspect, a stack of eye shields according to the disclosure includes a plurality of eye shields each having a frame with receivers located along the frame and latches located to engage the receivers, and spaced apart elevated support surfaces along and rising above an upper portion of the frame; and a lens installed on the frame and having lens apertures extending through the lens and aligned with the receivers of the frame, with the latches engaged with the receivers securing the lens to the frame.

The eye shields are stacked one on top of another with each of the eye shields oriented substantially parallel to one another with each of the elevated surfaces of an overlying one of the frames of the stack being slightly forward of a corresponding one of the elevated surfaces of the underlying frame of the stack, with each frame of each eye shield of the stack having a gap therebetween except at contact surfaces where the elevated support surfaces contact an adjacent lower surface of an overlying eye shield. The elevated support surfaces of the frames stabilize the stack of the eye shields for shipping and dispensing of the stack of the eye shields.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
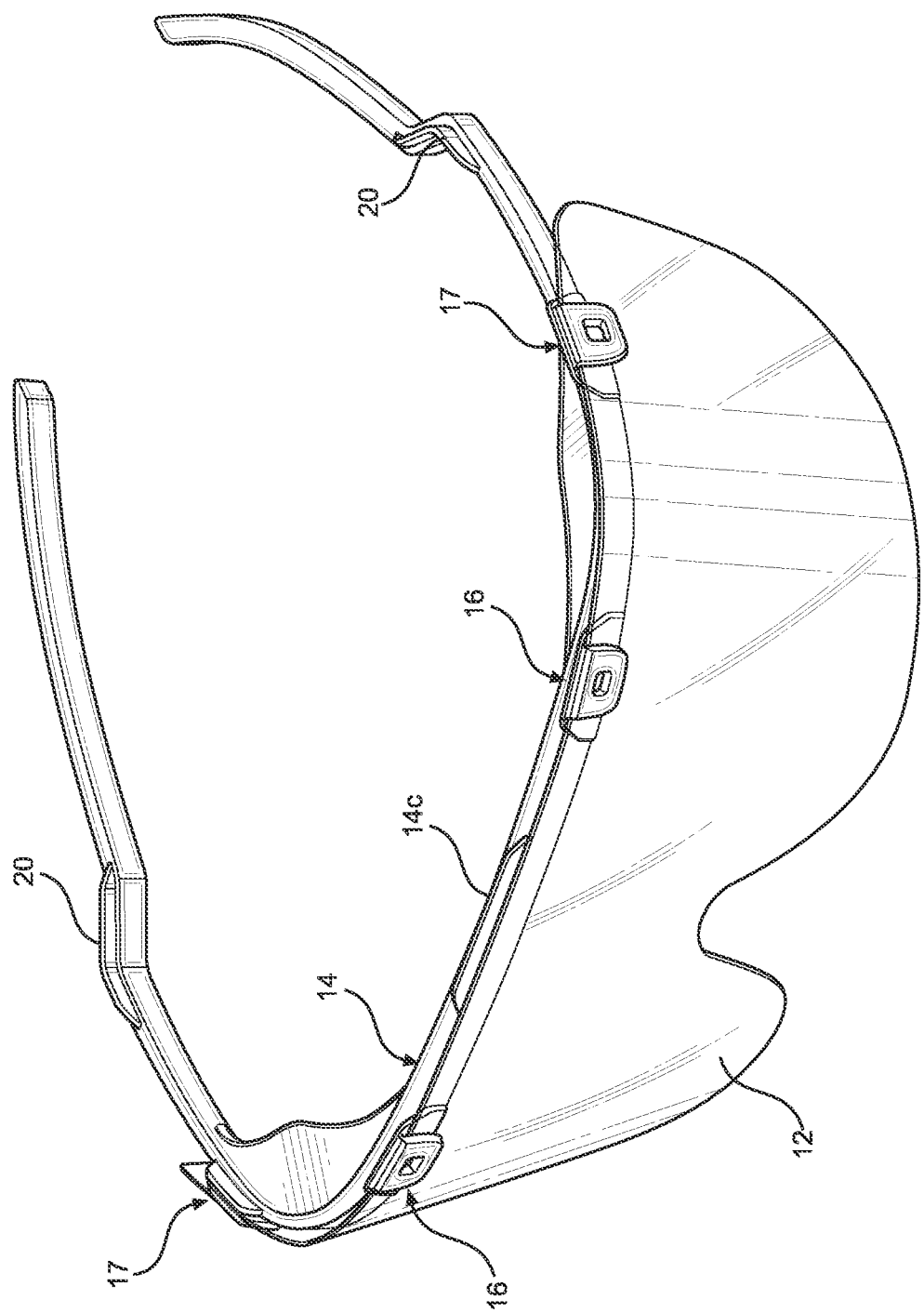
FIG. 1 is a perspective view of an eye shield according to the disclosure.
Figure 2:
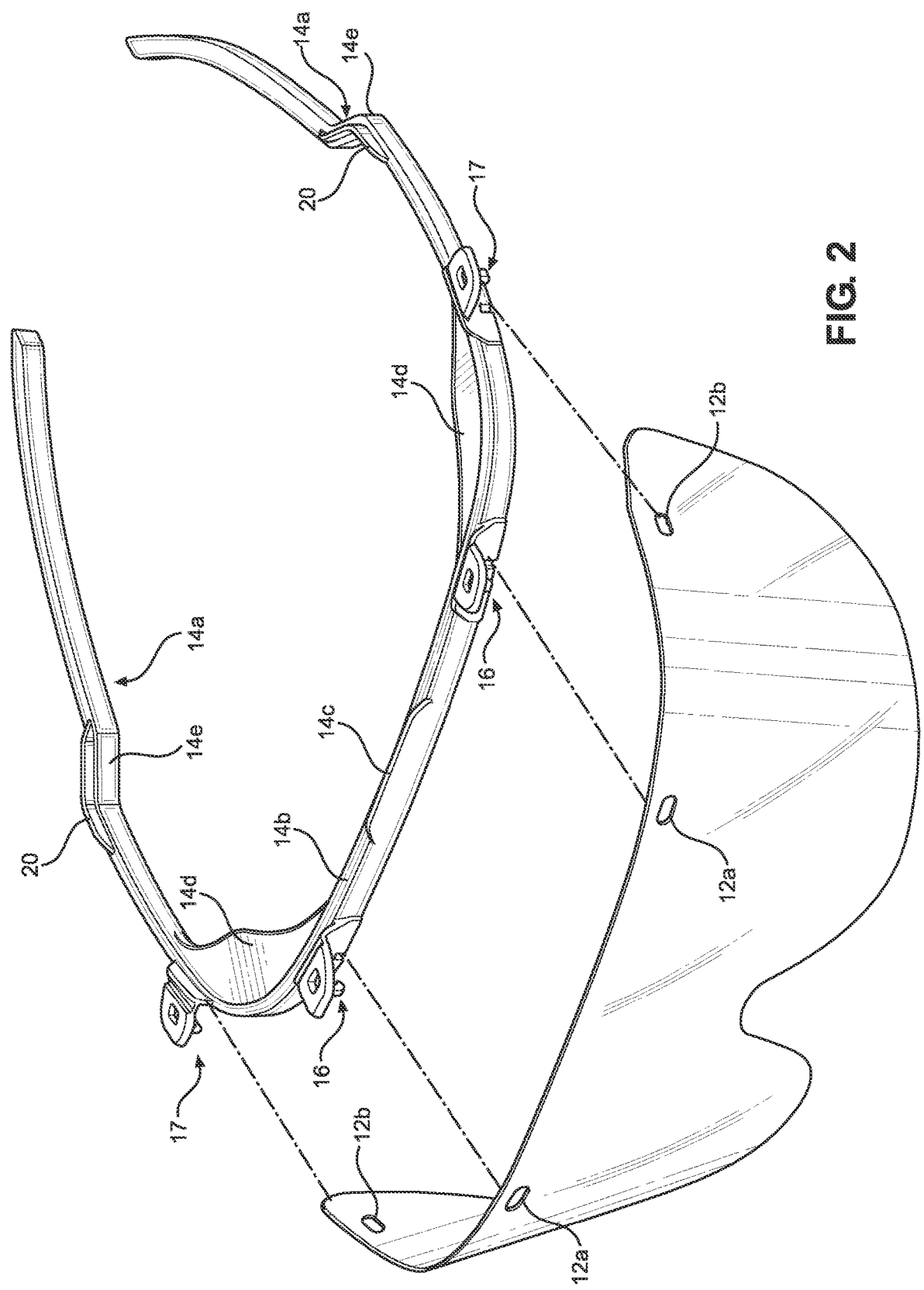
FIG. 2 is an exploded view thereof.

With reference to the drawings, the disclosure provides an eye shield 10. The eye shields 10 are desirably configured to facilitate vertical stacking of the eye shields 10 so that the eye shields 10 do not entangle so that a user can just grasp the top most eye shield from the stack and not have to handle underlying ones.

The appearance of the eye shields 10 is also configured to be aesthetically pleasing and includes various ornamental aspects and features.

The eye shield 10 has a lens 12 attached in a releasable snap-fit relationship to a frame 14 by hinged brow latches 16 and hinged temple latches 17 of the frame 14.

The lens 12 is preferably a one-piece plastic lens die cut from flat plastic film or other suitable lens material. The lens 12 includes a plurality of spaced apart lens apertures 12a and 12b defined adjacent an upper edge of the lens 12.

The frame 14 is preferably of molded plastic construction and has ear pieces 14a and a curved brow piece 14b. The brow piece 14b preferably has reduced material so as to flex for good fit, but may include an elevated central stiffener 14c and corner braces 14d to maintain desired rigidity. As described more fully below, the elevated stiffener 14c and other elevated structures of the frame 14 desirably aid in the stacking of the eye shields 10. The ear pieces 14a meet the brow piece 14b at junctures 14e that are desirably non-linear and angle the ear pieces 14a inwardly.

The brow piece 14b also includes brow receivers 18 and temple receivers 19 formed thereon configured to cooperate with the lens apertures 12a and 12b and the latches 16 and 17, respectively, as described more fully below.

The frame 14 also includes a plurality of elongate, narrow elevated members or ridges 20 defined along upper surfaces of the ear pieces 14a of the frame 14. As described in more detail below, the ridges 20 of the frames 14 cooperate to facilitate vertical stacking of the eye shields 10 and enable maintenance of the stacked eye shields 10 in a vertically stacked and substantially parallel relationship for shipping and dispensing of the eye shields 10 in the stacked relationship.

The hinged brow latches 16 are specially configured to cooperate with the receivers 18 and the lens apertures 12a and hold the lens 12 in place on the frame 14. The hinged brow latches 16 are also configured to be easily unlatched from the receiver 18 for removal of the lens 12, and re-latched for replacement of the lens 12 if desired. The hinged brow latches 16 are preferably of unitary plastic construction co-formed with the frame 14.

The hinged temple latches 17 are specially configured to cooperate with the receivers 19 and the lens apertures 12b and hold the lens 12 in place on the frame 14. The hinged temple latches 17 are also configured to be easily unlatched from the receivers 19 for removal of the lens 12, and re-latched for replacement of the lens 12 if desired. The hinged temple latches 17 are preferably of unitary plastic construction co-formed with the frame 14.

As explained more fully below, the hinged brow latches 16 and the hinged temple latches 17 are configured to rise above the frame 14 and to assist in stacking of the eye shields 10.

The hinged brow latches 16 and the hinged temple latches 17 are substantially similar, except as explained more fully below, the hinged temple latches 17 are even further configured to assist with stacking of the eye shields. The hinged brow latches 16 could be configured in the same manner, but it has been observed that the locations of the hinged brow latches 16 do not cause them to be involved in stacking of the eye shields in the same manner as the hinged temple latches 17.

Figure 11:
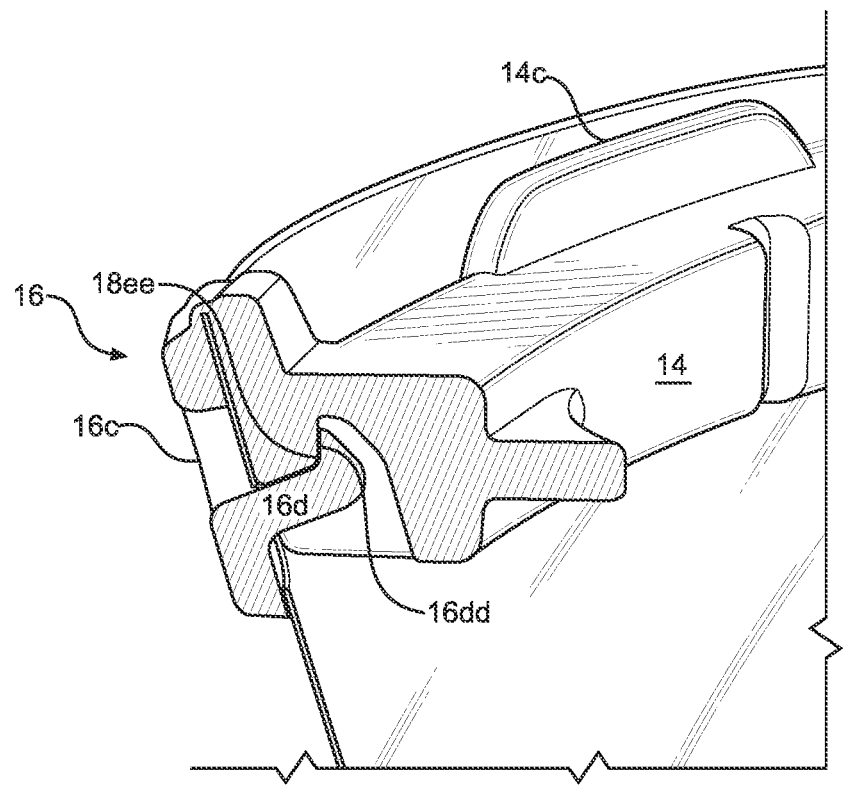
FIGS. 11-12 depict brow latches of the eye shields.
Figure 12:
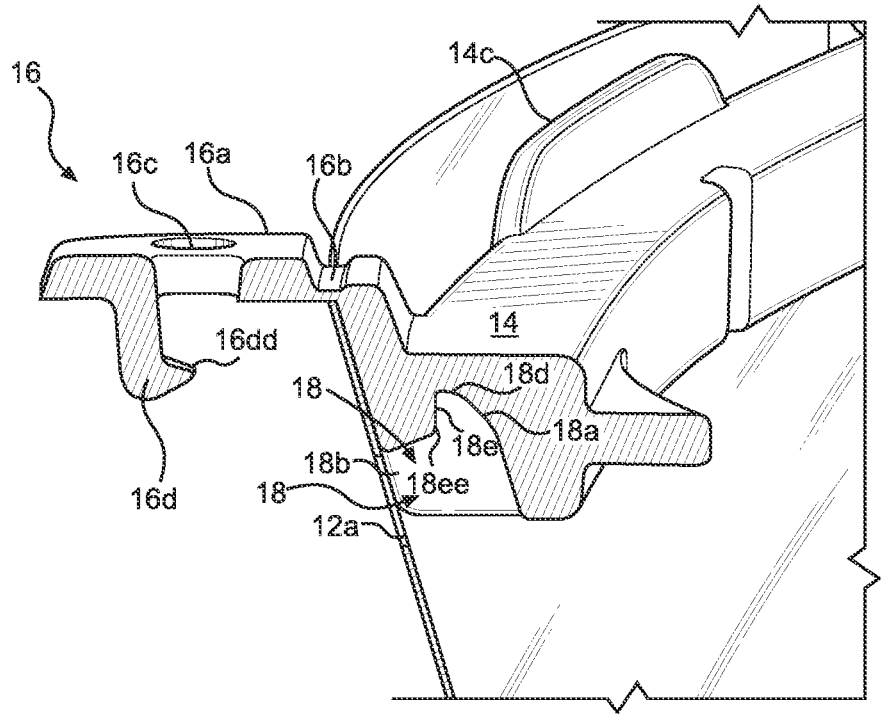
Figure 15:
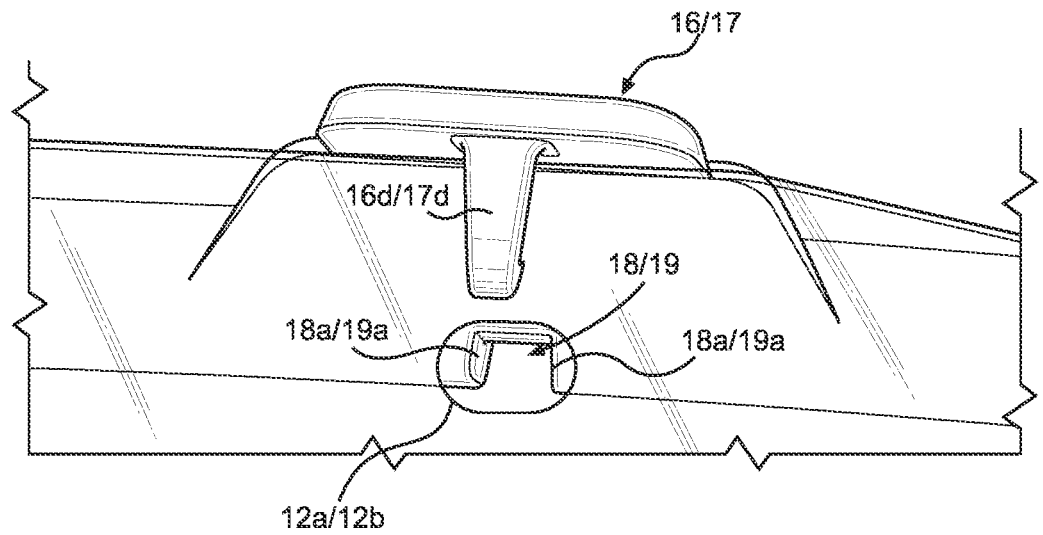
FIG. 15 depicts cooperation of the shield with the latches.

With additional reference to FIGS. 11-12 and 15, the hinged brow latches 16 include a flap 16a hingedly attached to an upper edge of the brow piece 14b as by a hinge 16b, which is preferably a living hinge. The flap 16a is desirably a thin, flat member configured to provide a continuous flat surface, except for a central void area or window 16c formed on the flap 16a. The window 16c provides desired aesthetics to the appearance of the hinged latch 16, and also enables desirable flexion to the flap 16a when force is applied to facilitate disengagement of the hinged latch 16 from the receiver 18. An elongate catch 16d is located to extend from an inner surface of the flap 16a and located below the window 16c and configured to extend at an upward angle into the receiver 18 to engage with the receiver 18 in a snap-fit relationship when the flap 16a is closed. The catch 16d includes a projecting tooth 16dd located and configured to engage the receiver 18.

Figure 13:
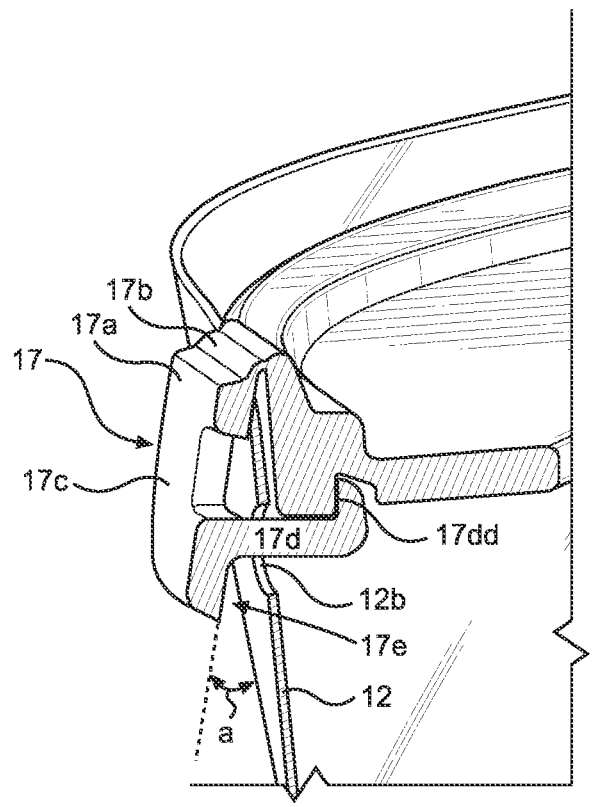
FIGS. 13-14 depict temple latches of the eye shields.
Figure 14:
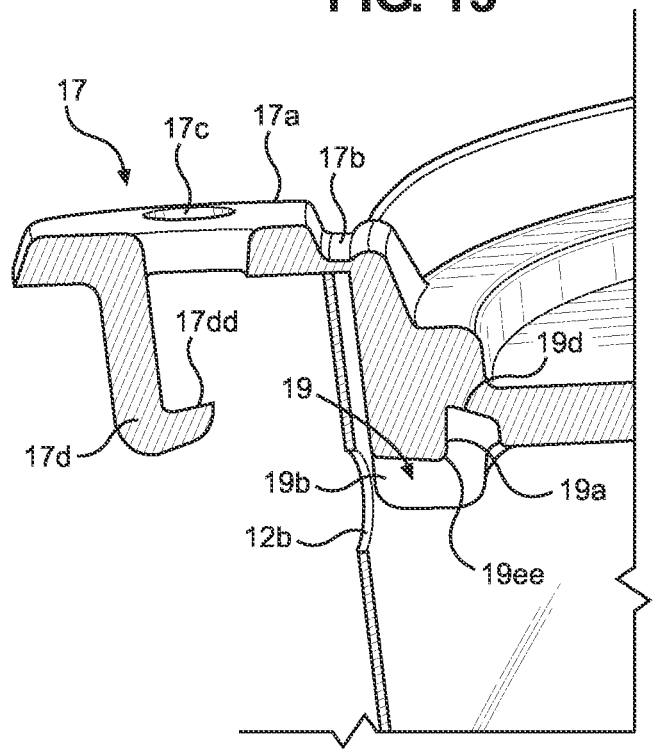

With reference to FIGS. 13-15, the hinged temple latches 17 include a flap 17a hingedly attached to an upper edge of the brow piece 14b as by a hinge 17b, which is preferably a living hinge. The flap 17a is desirably a thin, flat member configured to provide a continuous flat surface, except for a central void area or window 17c formed on the flap 17a. The window 17c provides desired aesthetics to the appearance of the hinged latch 17, and also enables desirable flexion to the flap 17a when force is applied to facilitate disengagement of the hinged latch 17 from the receiver 19. An elongate catch 17d is located to extend from an inner surface of the flap 17a and located below the window 17c and configured to extend at an upward angle into the receiver 19 to engage with the receiver 19 in a snap-fit relationship when the flap 19a is closed. The catch 17d includes a projecting tooth 17dd located and configured to engage the receiver 19.

As mentioned previously, the latches 16 and 17 are substantially similar, except the hinged temple latches 17 are configured to further assist with stacking of the eye shields beyond that which is provided by the latches 16. The difference between the hinge 17 and the hinge 16 is that the elongate catch 17d of the latch 17 is longer than the elongate catch 16d of the latch 16.

As such, and with reference to FIGS. 13-14, this causes the lowermost rear surface of the flap 17a to be spaced apart from the lens 12 and angled away from the lens 12 at an angle a to provide a pocket 17e. Angle a is typically from about 10 to about 15 degrees when the eye shields 10 are not stacked, with the angle a decreasing for stacked eye shields due to the weight of the stack. In explanation, when the eye shields 10 are stacked, the angle a may approach zero as the lens 12 may be touching the rear surface of the flap 17a, which allows the next lower adjacent frame/lens to nest into position. Once the frame 14 is removed from the stack, the angle a of the latches 17 of that frame will be around 13-14 degrees. The maximum angle of angle a for the latch 17 in the latched position is preferably about 15 degrees.

Figure 20:
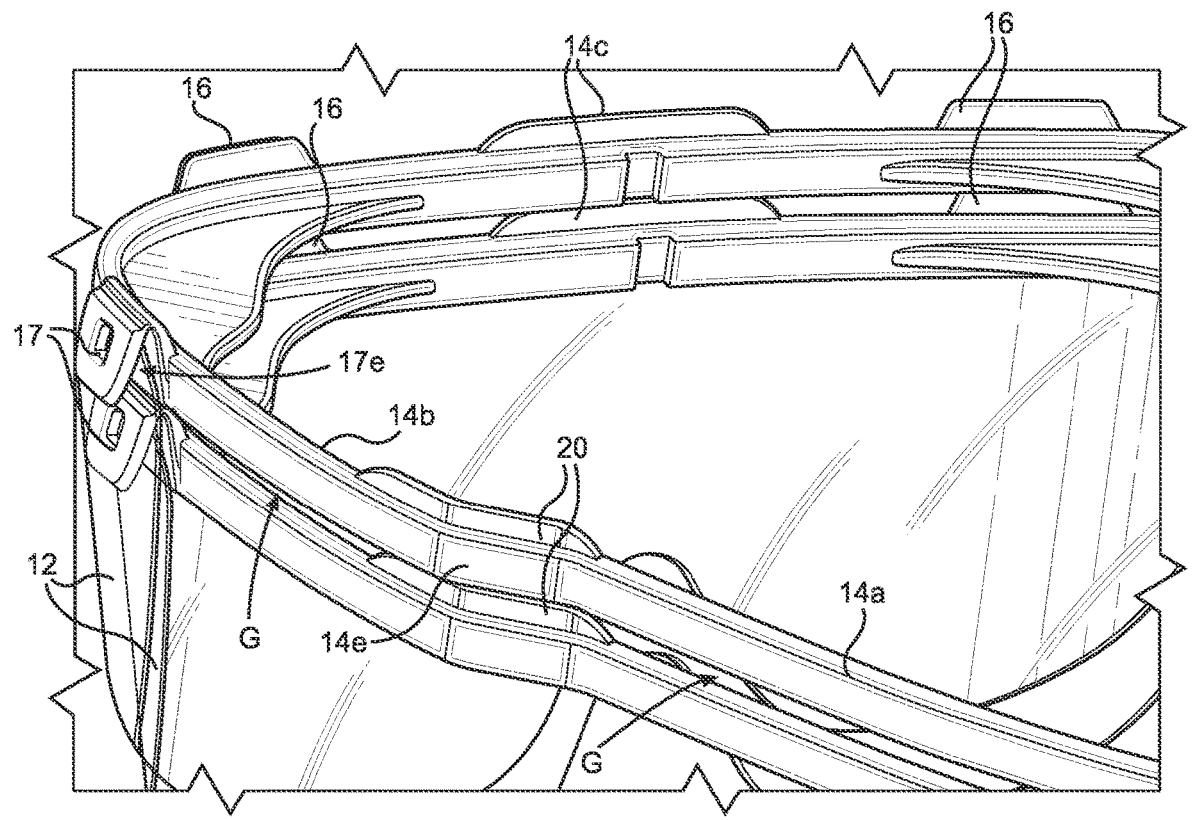
Figure 21A:
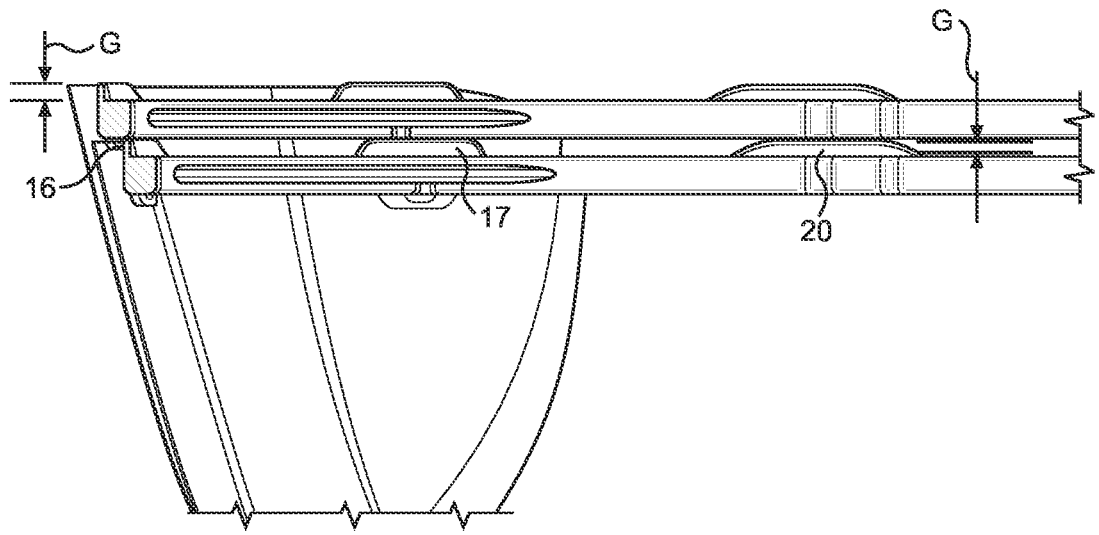
FIGS. 21A-21D show contact locations between stacked eye shields.
Figure 21B:
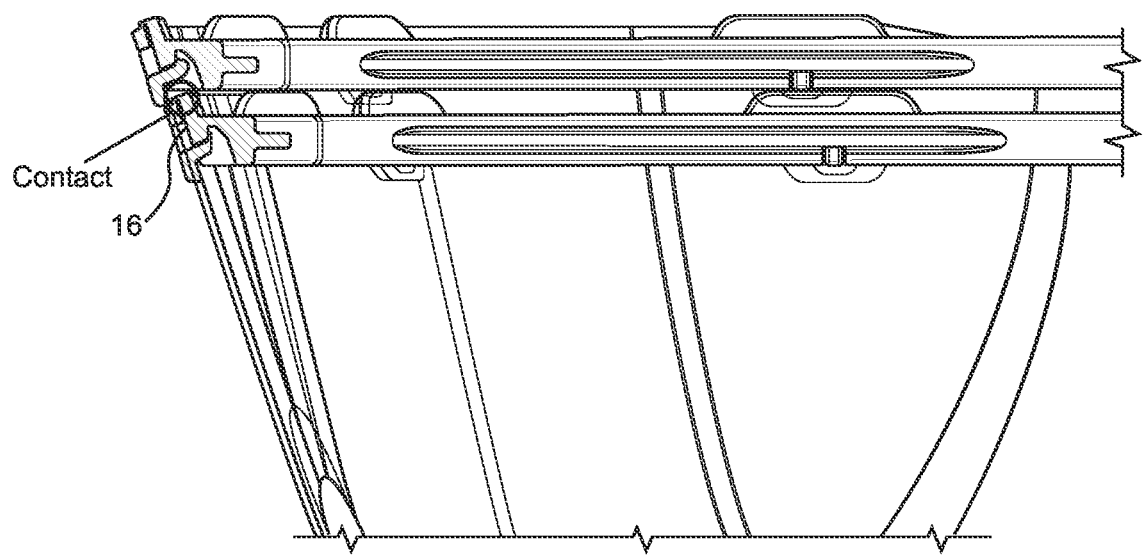
Figure 21C:
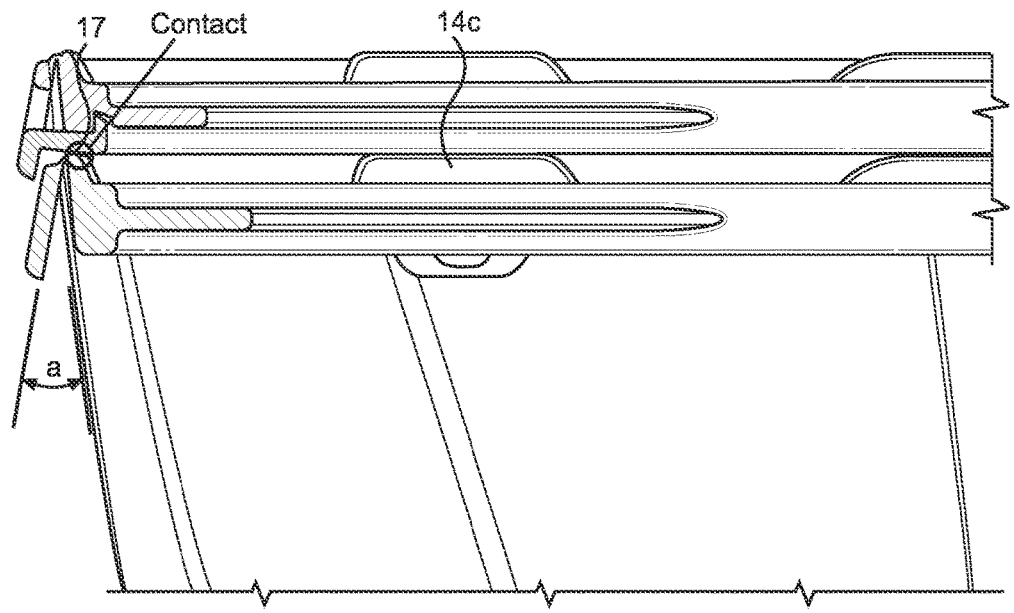
Figure 21D:
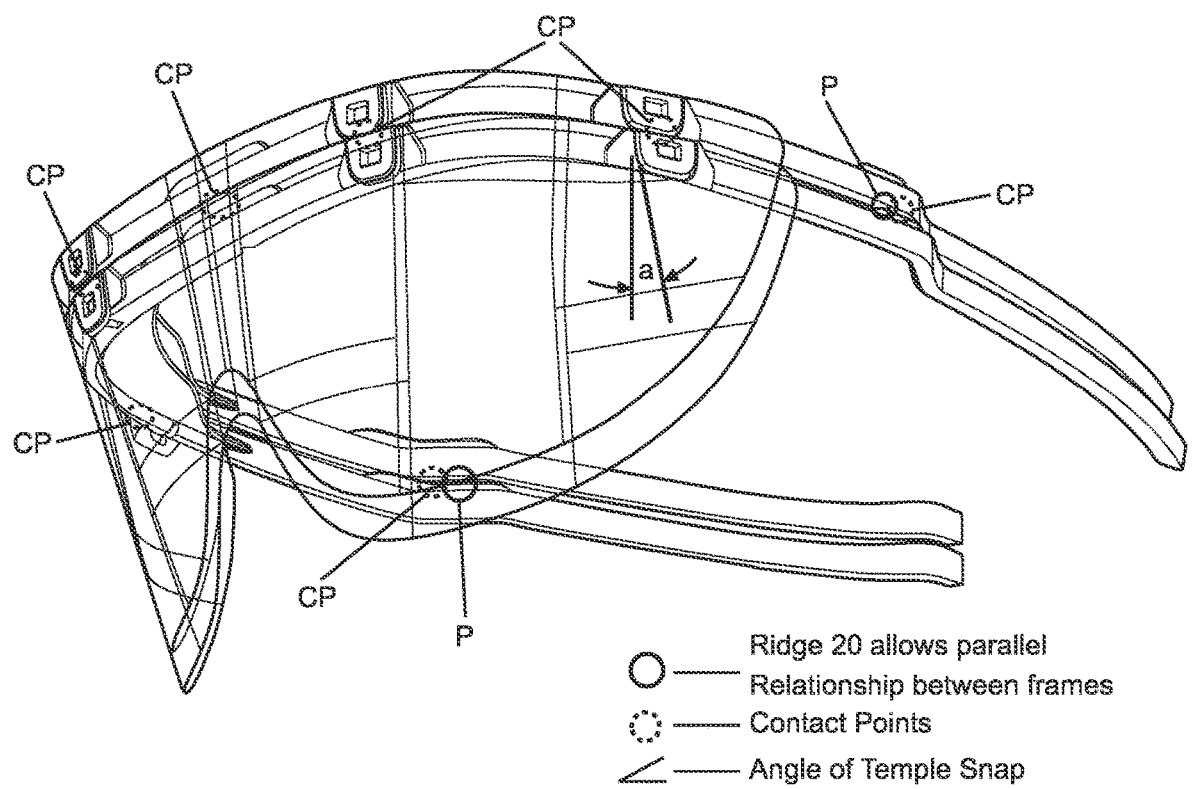

As shown in FIG. 20, the pocket 17e is configured to receive the underlying latch 17 of an underlying eye shield 10 in a stack of the eye shields 10. The pocket 17e also advantageously provides room or clearance for the lens 12 to flex for stacking of the eye shields 10 to reduce stresses on the lens 12 due to stacking.

The receivers 18 and are spaced and located to correspond to the locations of the lens apertures 12a. As shown in FIGS. 11-12 and 15, the receivers 18 define an elongate cavity and are formed along a lower frontal edge of the curved brow piece 14b. The receivers 18 are open at the bottom and the front with a rear wall 18a, opposite side walls 18b, sloped entrance wall 18c, and rear ceiling 18d. A catch wall 18e is located between the entrance wall 18c and the rear ceiling 18d and is preferably substantially vertical. A lower portion of the catch wall 18e provides a catch surface 19ee for cooperating with the latch 16.

The receivers 19 correspond in configuration to the receivers 18 and are spaced and located to correspond to the locations of the lens apertures 12b. As shown in FIGS. 13-15, the receivers 19 define an elongate cavity and are formed along lower temporal edges of the curved brow piece 14b. The receivers 19 are open at the bottom and the front with a rear wall 19a, opposite side walls 19b, sloped entrance wall 19c, and rear ceiling 19d. A catch wall 19e is located between the entrance wall 19c and the rear ceiling 19d and is preferably substantially vertical. A lower portion of the catch wall 19e provides a catch surface 19ee for cooperating with the latch 17.

During assembly of the eye shield 10, the lens 12 is located so that the apertures 12a of the lens 12 overlie the receivers 18 and the apertures 12b overlie the receivers 19. The hinged brow latches 16 are likewise located to engage the receivers 18 and the hinged temple latches 17 are located to engage the receivers 19.

To engage the latch 16 with the receiver 18, the flap 16a is rotated so as to pass the catch 16d into the receiver 18 through the aligned lens aperture 12a and opening of the receiver 18 located between the side walls 18b of the receiver 18. As will be noted, the catch 16d is inclined to match the slope of the sloped entrance wall 18c, which angle is preferably from about 20 to about 40 degrees. The catch 16d has a length configured so that when the flap 16a is flush with the lens 12 the tooth 16dd snugly engages the catch surface 18ee in a snap-fit frictional relationship and remains engaged with the catch surface 18ee unless force is applied as described herein to disengage the tooth 16dd from the catch surface 18ee.

If it is desired to disengage the latch 16 from the receiver 18 so as to be able to remove the lens 12 from the frame 14, a lower edge of the flap 16a may be grasped, as by a fingernail or the like, and the lower edge of the flap 16a flexed rearward slightly to disengage the tooth 16dd from the catch surface 18ee. In this regard the window 16c of the flap 16a enables desirable flexion to the flap 16a when force is applied to facilitate disengagement of the hinged latch 16 from the receiver 18. The flexion provided by the window 16c avoids permanent bending or the flap 17a.

The sloped configuration of the catch 16d and the entrance wall 18c of the receiver 18 and the configurations of the tooth 16dd and the catch surface 18ee also cooperate such that only a very small amount of flexion of the flap 16a is needed to disengage the latch 16 from the receiver 18, yet the latch 16 otherwise remains snugly engaged in the receiver 18. Synergistic with this is the configuration of the catch 16d below the window 16c such that focused force is applied to a lower edge of the flap 16a and the flap 16a is not permanently deformed such that the flap 16a returns to its original flat shape to enable the latch 16 to be repeatably engageable and disengageable with the receiver 18.

In a similar manner. to engage the latch 17 with the receiver 19, the flap 17a is rotated so as to pass the catch 17d into the receiver 19 through the aligned lens aperture 12b and opening of the receiver 19 located between the side walls 19b of the receiver 19. As will be noted, the catch 17d is inclined to match the slope of the sloped entrance wall 19c, which angle is preferably from about 20 to about 40 degrees. As noted above, the catch 17d has a length longer than that of the catch 16d so that the lowermost rear surface of the flap 17a is apart from the lens 12 and angled away from the lens 12 to provide the pocket 17e. However, as will be noted in FIG. 13, the uppermost portion of the flap 17a above the window 17c engages the lens 12 so that the tooth 17dd is in tension and snugly engages the catch surface 19ee in a snap-fit frictional relationship and remains engaged with the catch surface 19ee unless force is applied as described herein to disengage the tooth 17dd from the catch surface 17ee.

If it is desired to disengage the latch 17 from the receiver 19 so as to be able to remove the lens 12 from the frame 14, a lower edge of the flap 17a may be grasped, as by a fingernail or the like, and the lower edge of the flap 17a flexed rearward slightly to disengage the tooth 17dd from the catch surface 19ee. In this regard the window 17c of the flap 17a enables desirable flexion to the flap 17a when force is applied to facilitate disengagement of the hinged latch 17 from the receiver 19. The flexion provided by the window 17c avoids permanent bending or the flap 17a.

The sloped configuration of the catch 17d and the entrance wall 19c of the receiver 19 and the configurations of the tooth 17dd and the catch surface 19ee also cooperate such that only a very small amount of flexion of the flap 17a is needed to disengage the latch 17 from the receiver 17, yet the latch 17 otherwise remains snugly engaged in the receiver 19. Synergistic with this is the configuration of the catch 17d below the window 17c such that focused force is applied to a lower edge of the flap 17a and the flap 17a is not permanently deformed such that the flap 17a returns to its original flat shape to enable the latch 17 to be repeatably engageable and disengageable with the receiver 19.

Figure 16:
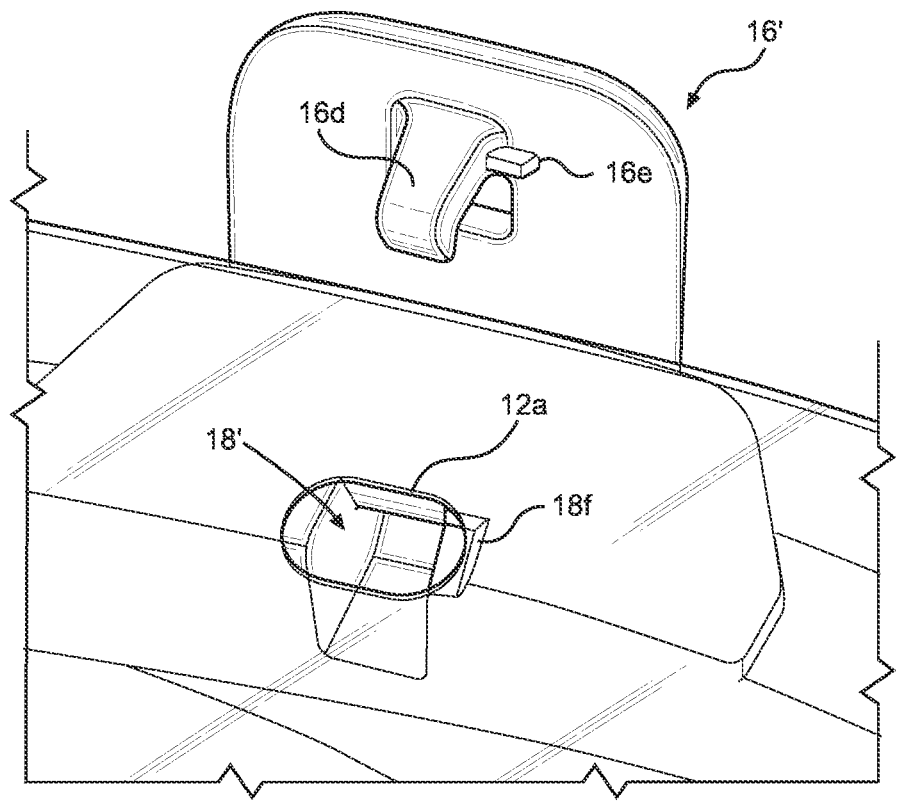
FIGS. 16-17 depict an alternate embodiment of a latch according to the disclosure.
Figure 17:
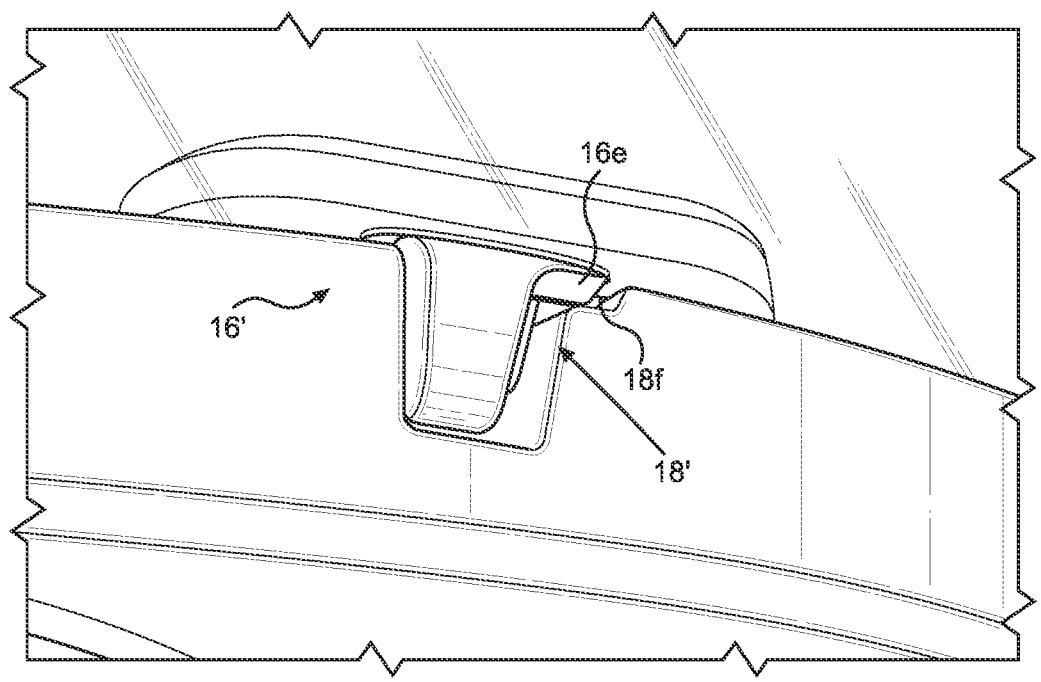
Figure 18:
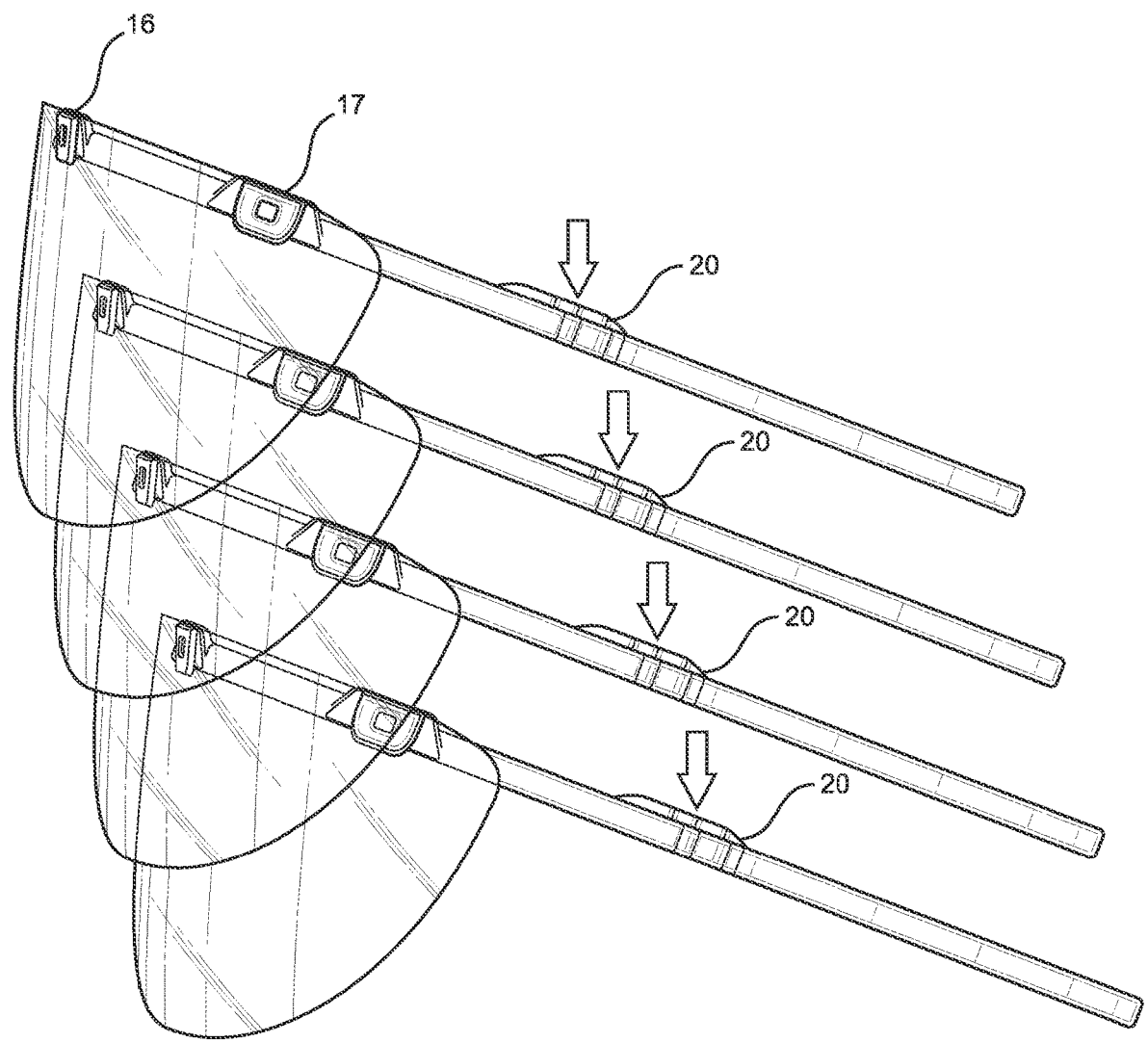
FIGS. 18-20 depict stacking of the eye shields.
Figure 19:
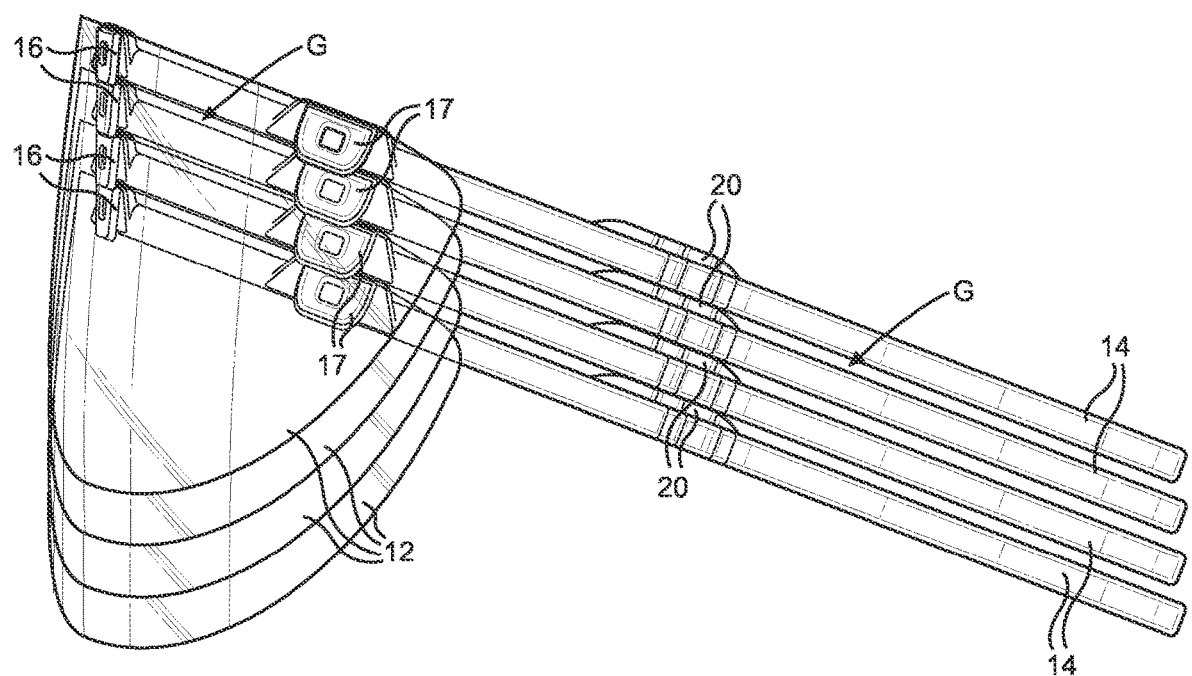

With reference to FIGS. 16-17 there is shown an alternative embodiment of a receiver 18' and a latch 16'. It will be appreciated that the modifications shown herein may also be applied to the latch 17 and the receiver 19, but it has been observed that the alternate embodiment is best suited for use in place of the receiver 18 and latch 16.

The latch 16' is substantially similar to the latch 16, except it includes a rib 16e extending outwardly from the catch 16d. The receiver 18' is substantially similar to the receiver 18, except it includes a pocket 18f defined to snugly receive the rib 16e. The rib 16e received in the pocket 18f serves to inhibit the lens 12 from shifting side-to-side FIGS. 18-23 depict vertical stacking of the eye shields 10 and the stacking ridges 20. The ridges 20 of the frames 14 cooperate to facilitate vertical stacking of the eye shields 10 and enable maintenance of the stacked eye shields 10 in a vertically stacked relationship for shipping and dispensing of the eye shields 10 in the stacked relationship.

In addition, the elevated upper surfaces of the latches 16 and the latches 17 aid in stacking of the eye shields 10. Also, as seen in FIG. 20, the pocket 17e of the latch 17 is configured to receive the underlying latch 17 of an underlying eye shield 10 in a stack of the eye shields 10. The pocket 17e also advantageously provides room or clearance for the lens 12 of the underlying eye shield 10 to flex for stacking of the eye shields 10 to reduce stresses on the lens 12 due to stacking. The pocket 17e also helps to inhibit the eye shields 10 from shifting and becoming entangled.

Figure 22:
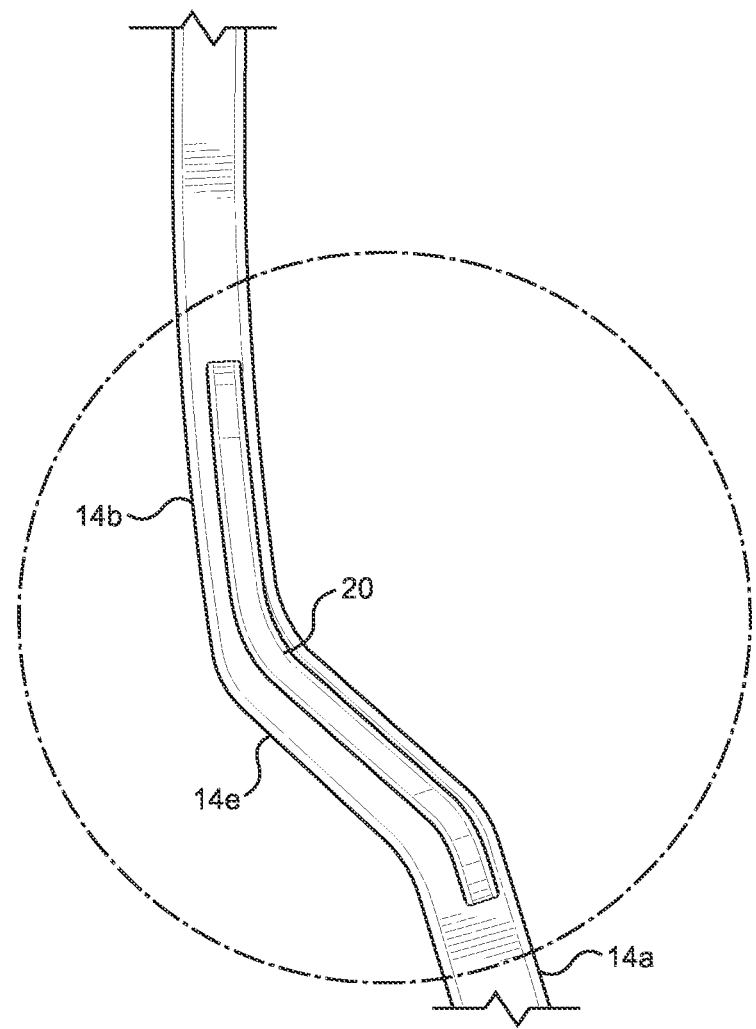
FIGS. 22-23 depict stacking ridges of the eye shields.
Figure 23:
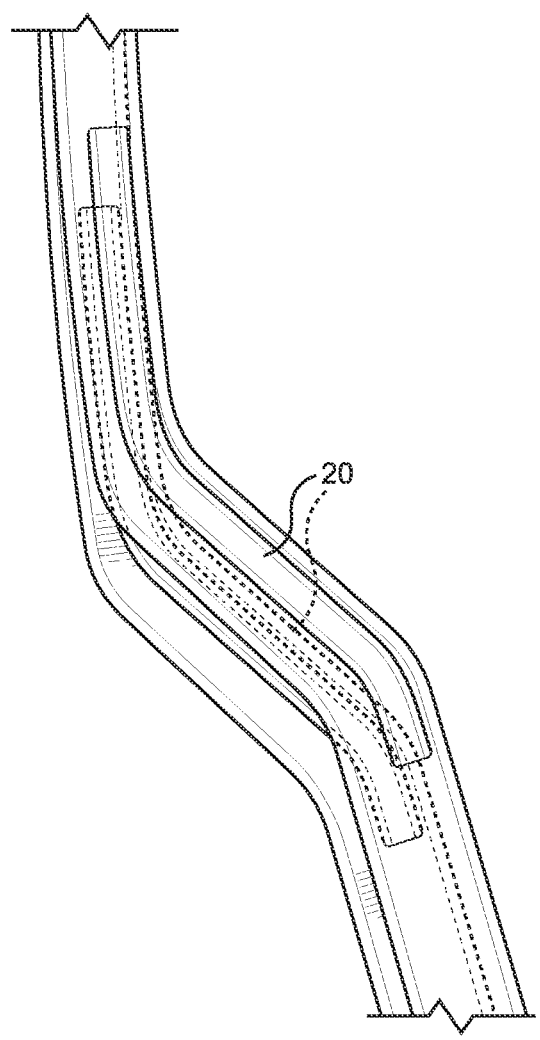

With additional reference to FIGS. 22-23, the ridges 20 are defined on an upper surface of the frame 14 at the non-linear juncture 14e of each ear piece 14a to the brow piece 14b, so as to span along a portion of the ear piece 14a, the brow piece 14b and the juncture 14e. The ridges 20 are elongate, narrow ridges that define a crooked raised line along the top of the frame 14. The manner of stacking of the ridges 20 also inhibits the eye shields 10 in the stack from shifting and becoming entangled so that a user can just grasp the top most eye shield from the stack to remove it from the stack and not have to handle underlying ones.

Figure 3:
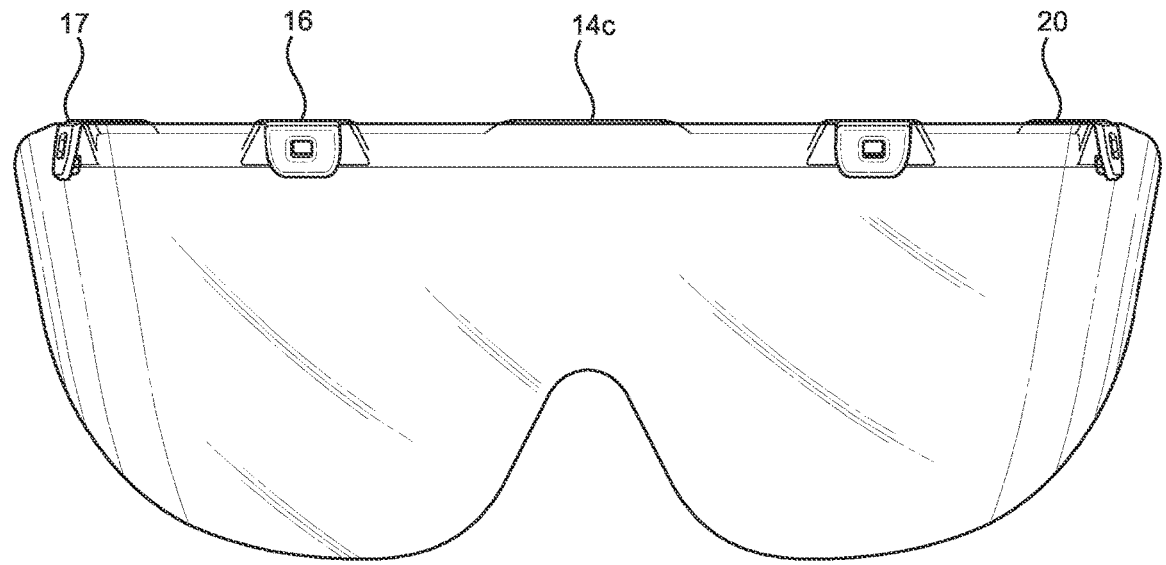
FIG. 3 is a frontal view thereof.
Figure 4:
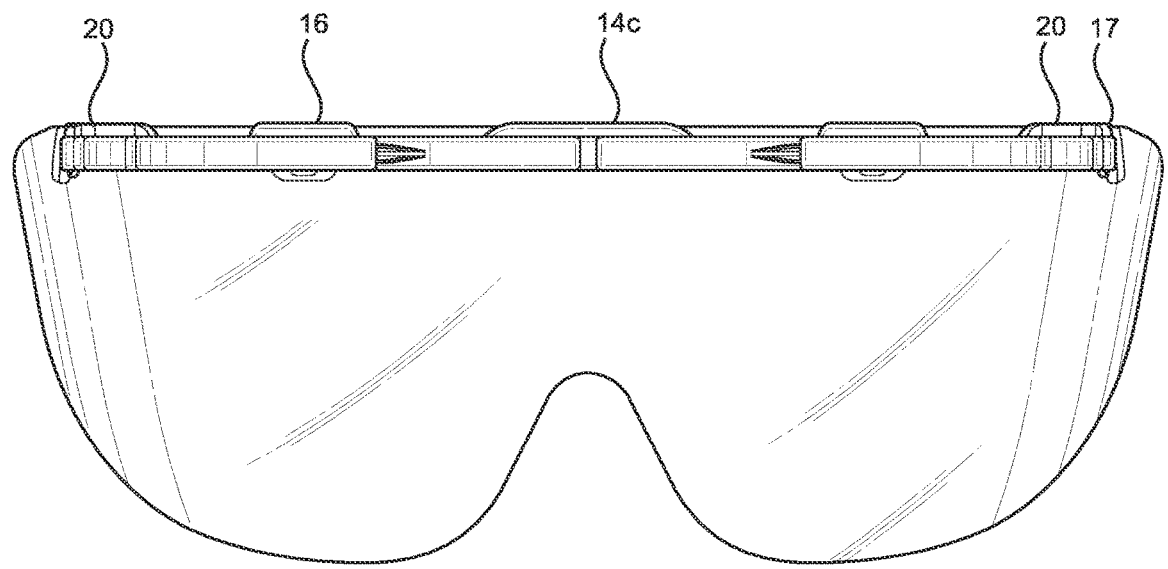
FIG. 4 is a rear view thereof.
Figure 5:
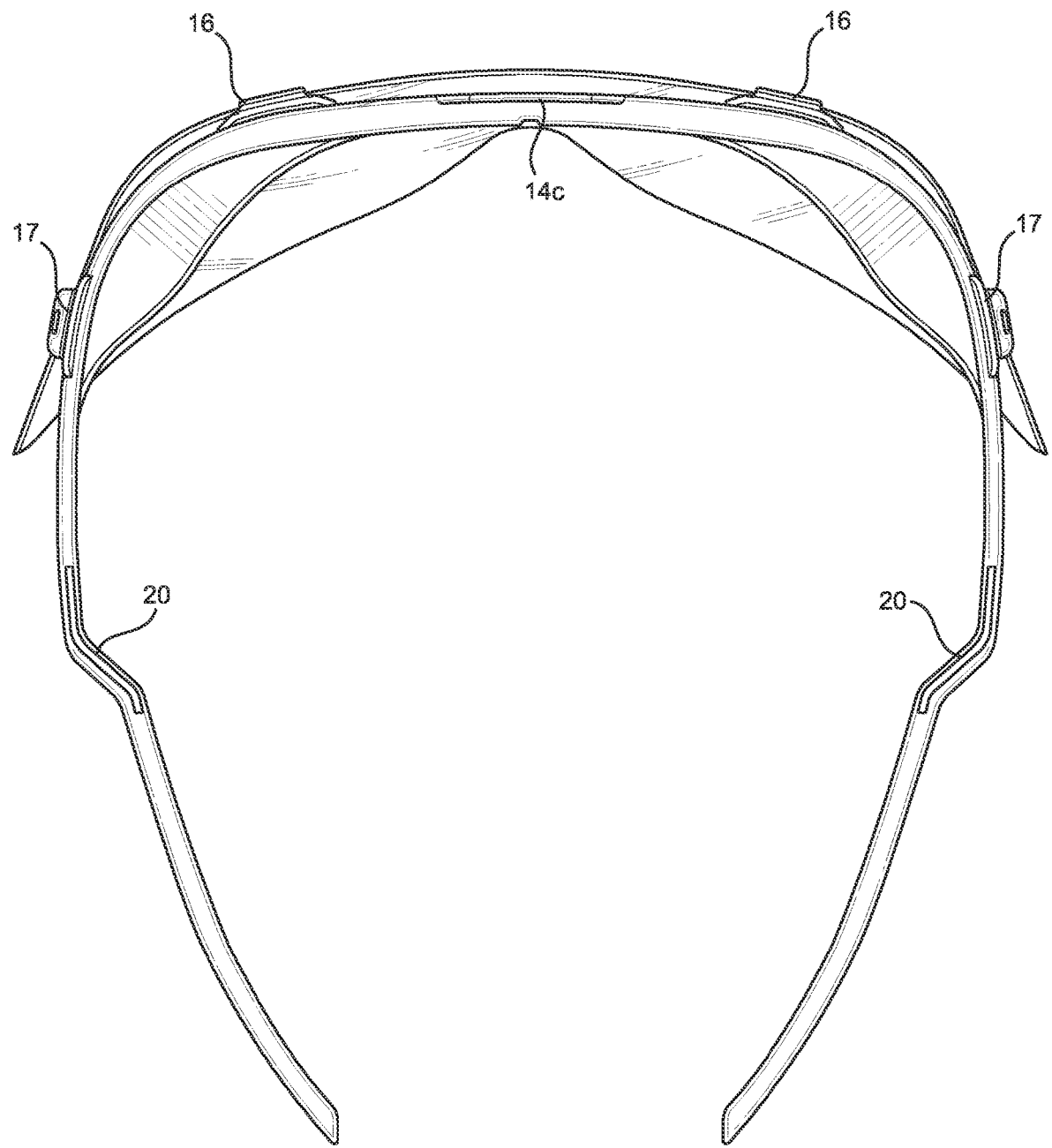
FIG. 5 is a top view thereof.
Figure 6:
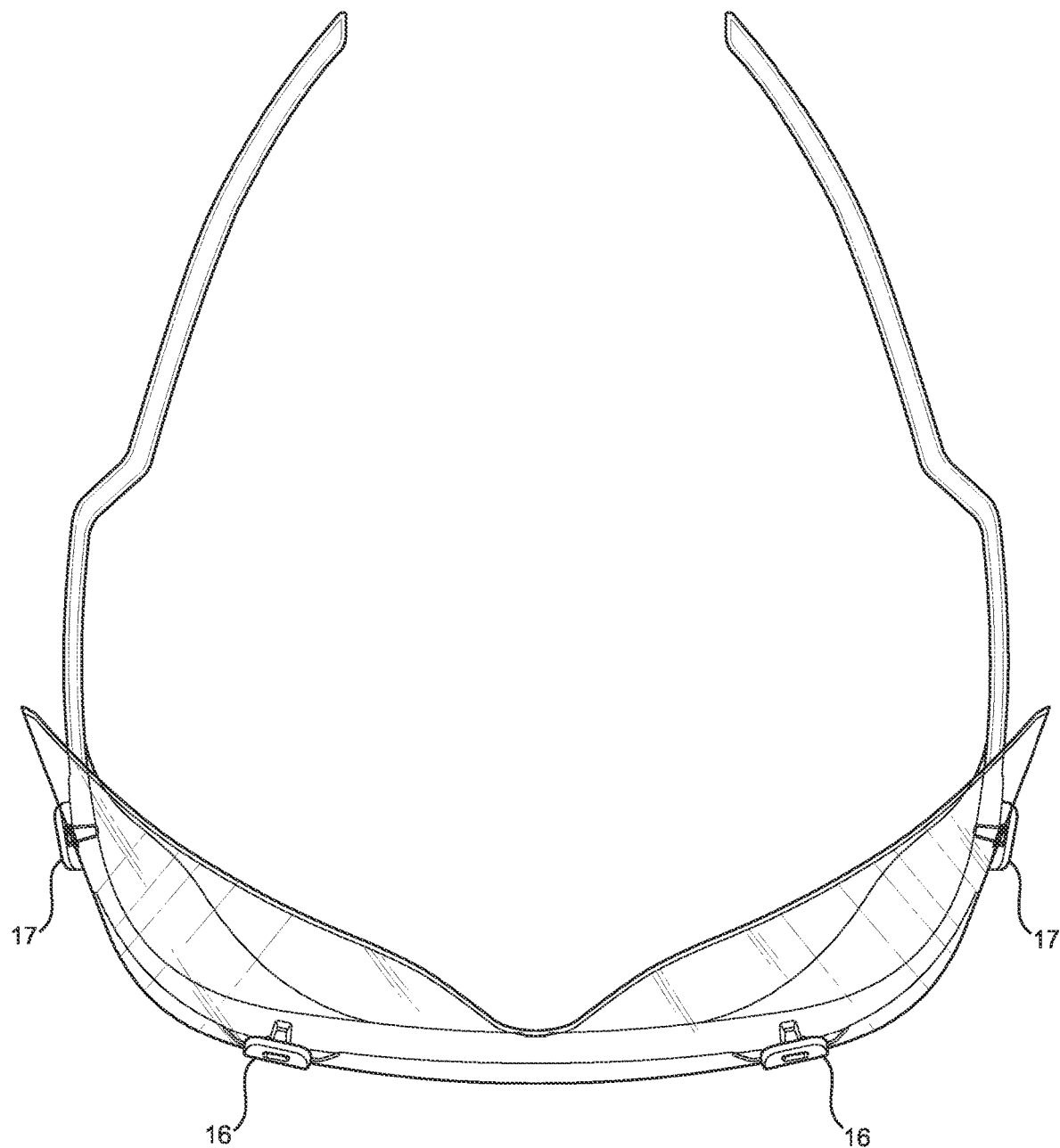
FIG. 6 is a bottom view thereof.
Figure 7:
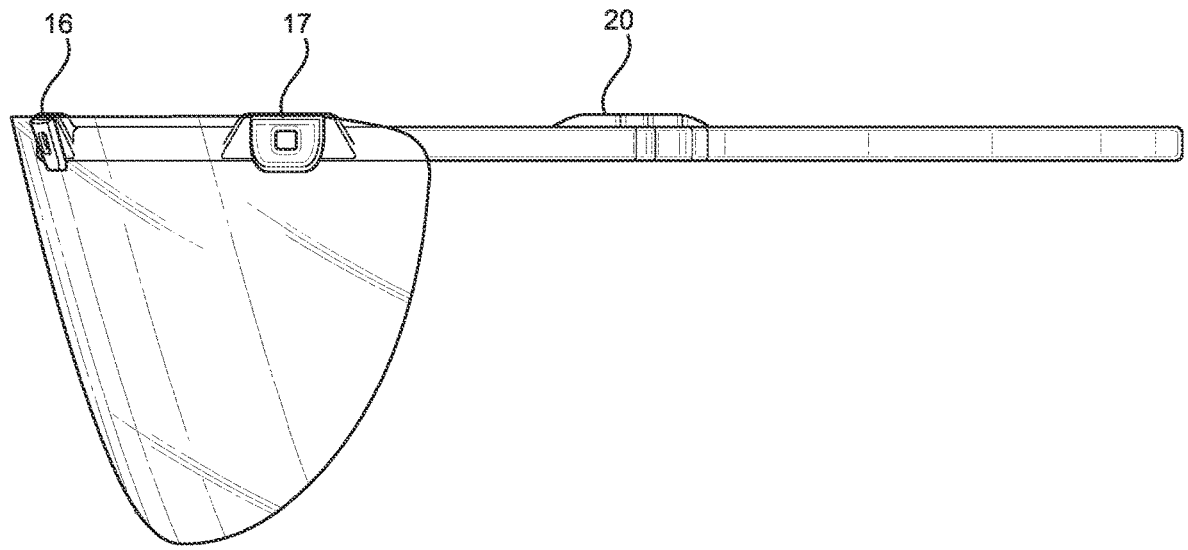
FIG. 7 is a left-side view thereof.
Figure 8:
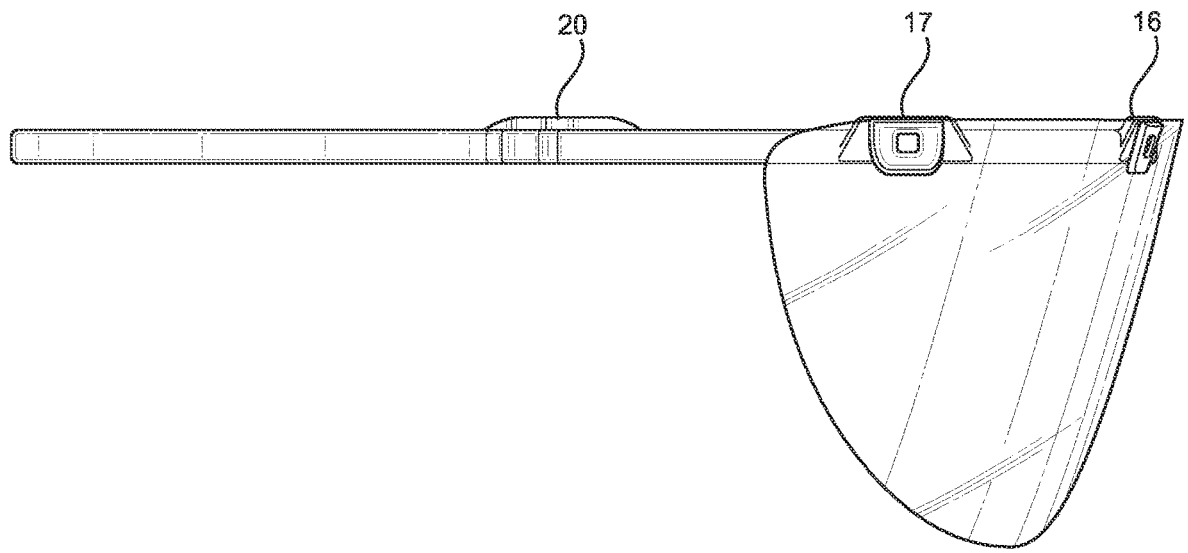
FIG. 8 is a right-side view thereof.
Figure 9:
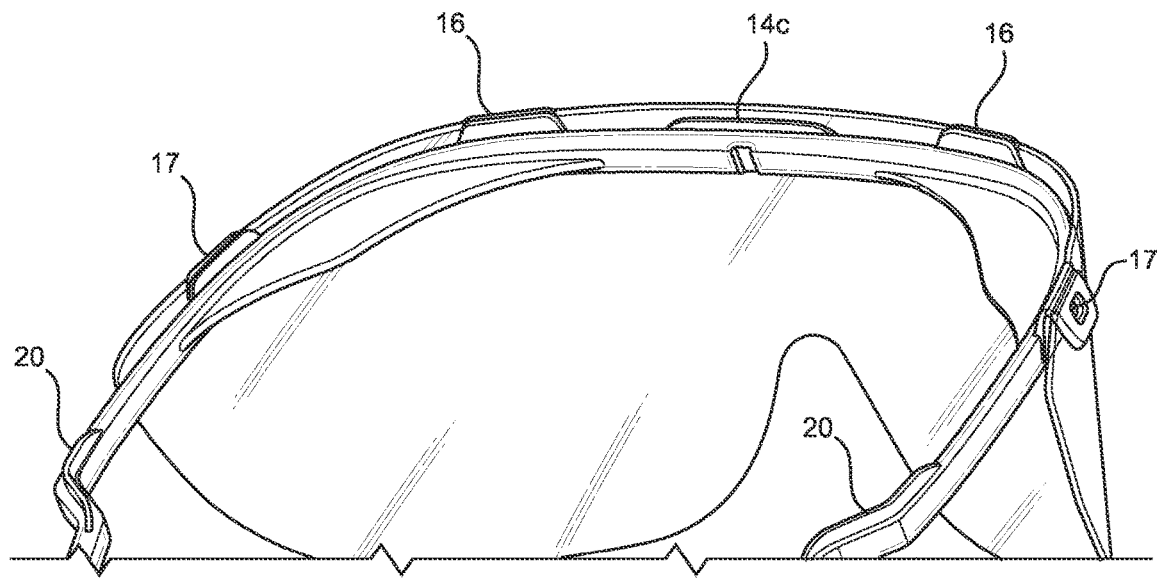
FIGS. 9-10 depict latches of the eye shields.
Figure 10:
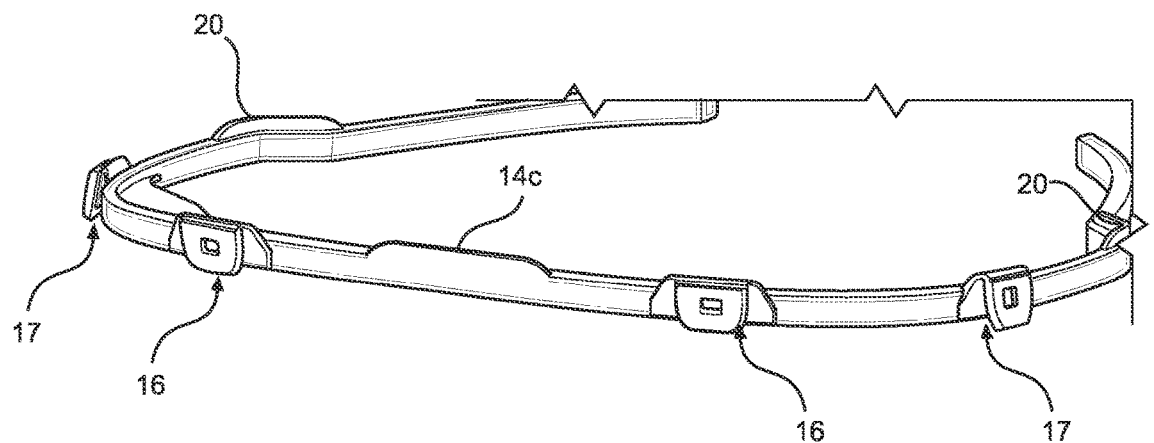

Returning now to FIGS. 3 and 4, it will be appreciated that the uppermost surfaces of the latches 16, the latches 17, the elevated stiffener 14c, and the ridges 20 all lie in a common plane elevated above the frame 14. As such, the latches 16, the latches 17, the elevated stiffener 14c, and the ridges 20 of adjacent ones of the eye shields 10 in a stack are contact surfaces between the stacked eye shields 10.

As a result, each frame 14 of each eye shield 10 of the stack has a gap G therebetween except at the elevated contact surfaces provided by the latches 16, the latches 17, the elevated stiffener 14c, and the ridges 20 of the lower eye shield which contact and support the lower surface of the frame 14 of the overlying eye shield 10 at contact points CP, as shown in FIGS. 21A-21D. Thus, the elevated contact surfaces provided by the latches 16, the latches 17, the elevated stiffener 14c, and the ridges 20 of the frames 14 stabilize the stack of the eye shields for shipping and dispensing of the stack of the eye shields.

As depicted in FIGS. 18-20 and 21A-21D, in stacking of the eye shields 10, the stack is substantially vertical and the eye shields 10 are aligned to be substantially parallel P in a stack, but do not directly vertically stack. This is because of the thickness of the lenses 12 and that each upper lens 12 in a stack overlaps the underlying lens 12. As such, each latch 16, latch 17, stiffener 14c, and upper ridge 20 in the stack is slightly forward of the latch 16, latch 17, stiffener 14c, and underlying ridge 20.

Providing the ridges 20 at the temple locations of the frame 14 enables weight loading of the eye shields to be at locations away from or remote from the lenses 12 to avoid stresses to the lenses 12 from stacking of the eye shields 10. Thus, the ridges 20 provide the primary weight bearing locations for the stack of eye shields.

Figure 24:
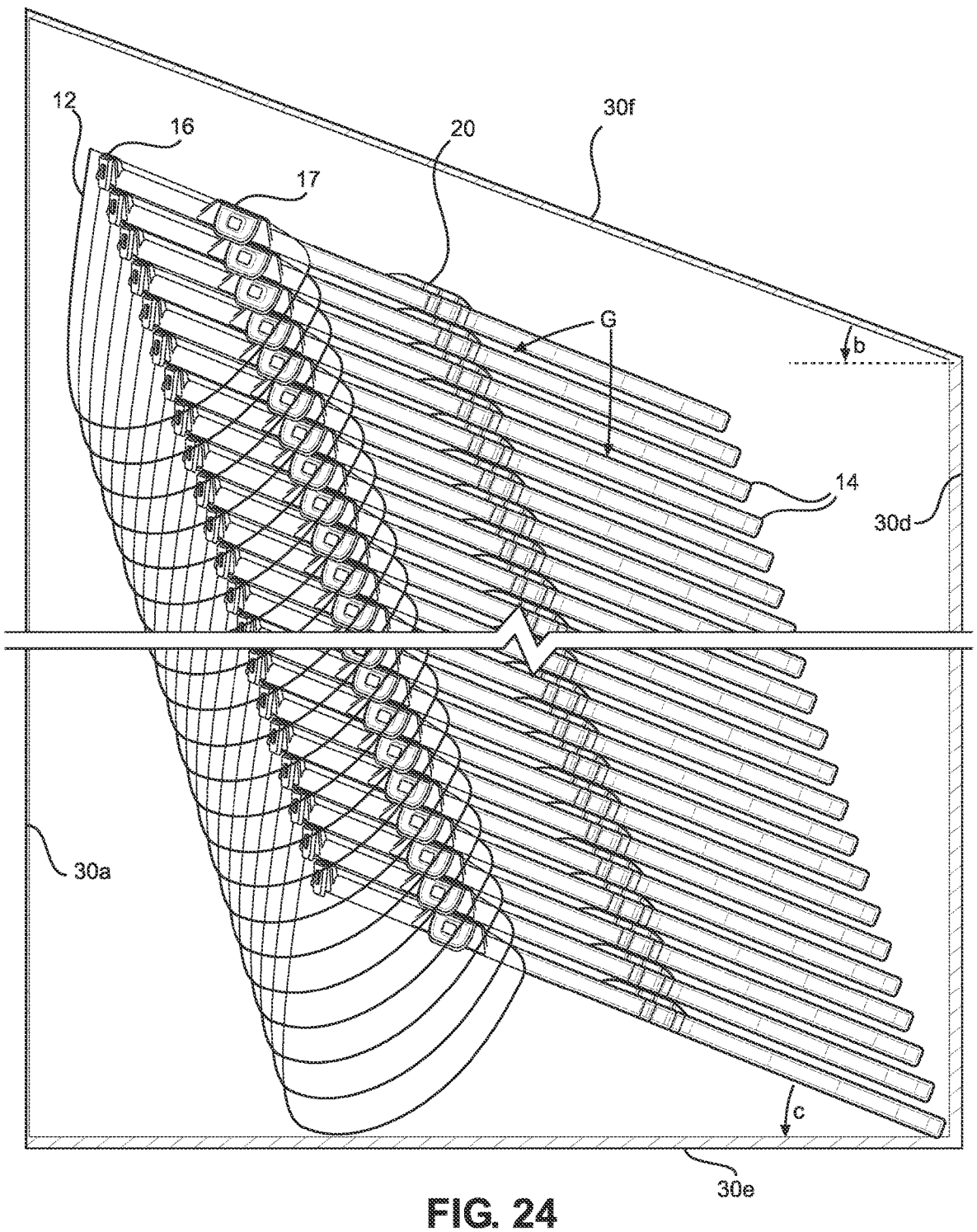
FIG. 24 shows the eye shields stacked for shipping and display in a specially configured container suitable for shipping and dispensing of the eye shields.
Figure 25:
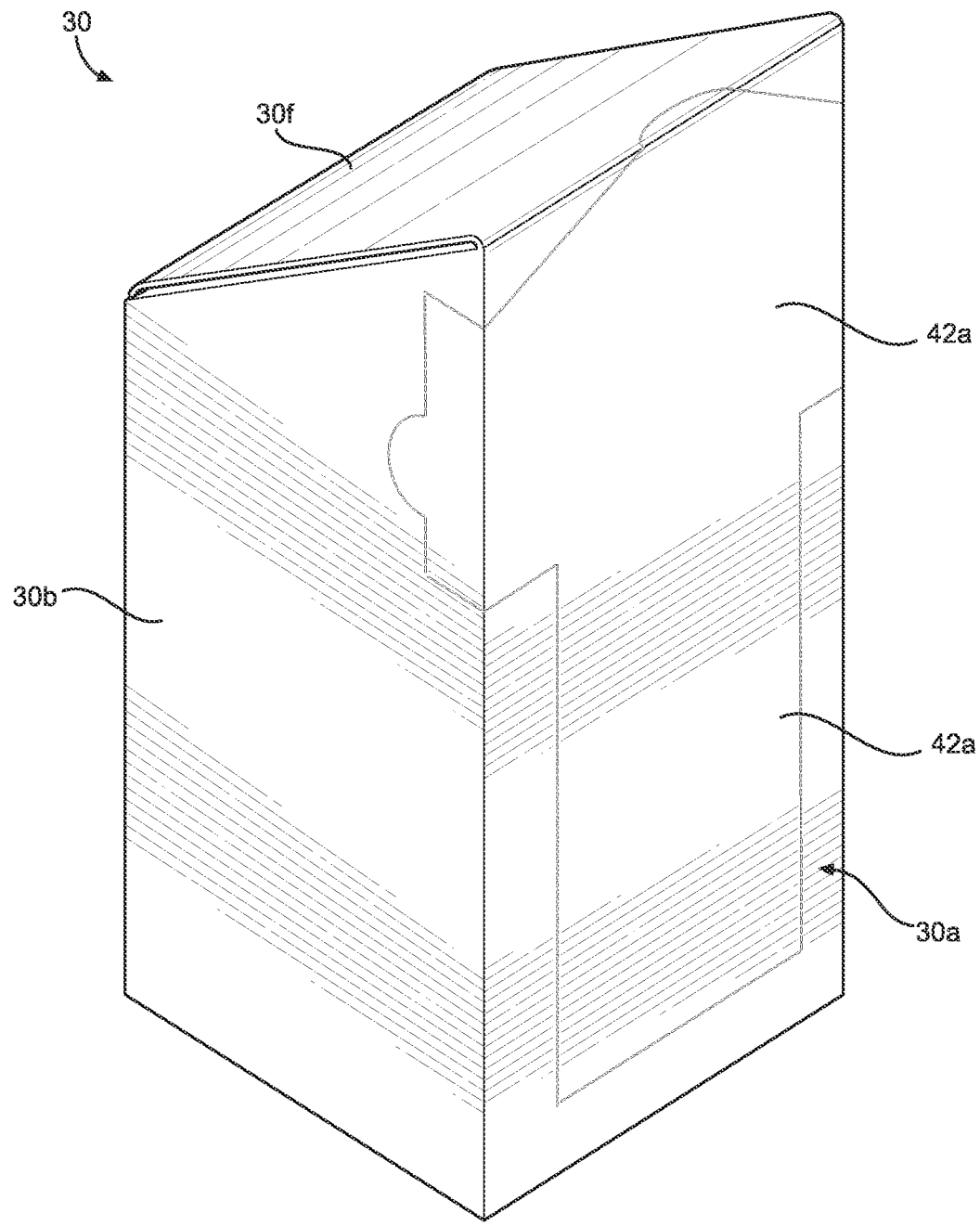
FIG. 25 shows the container configured for shipping of the eye shields.
Figure 26:
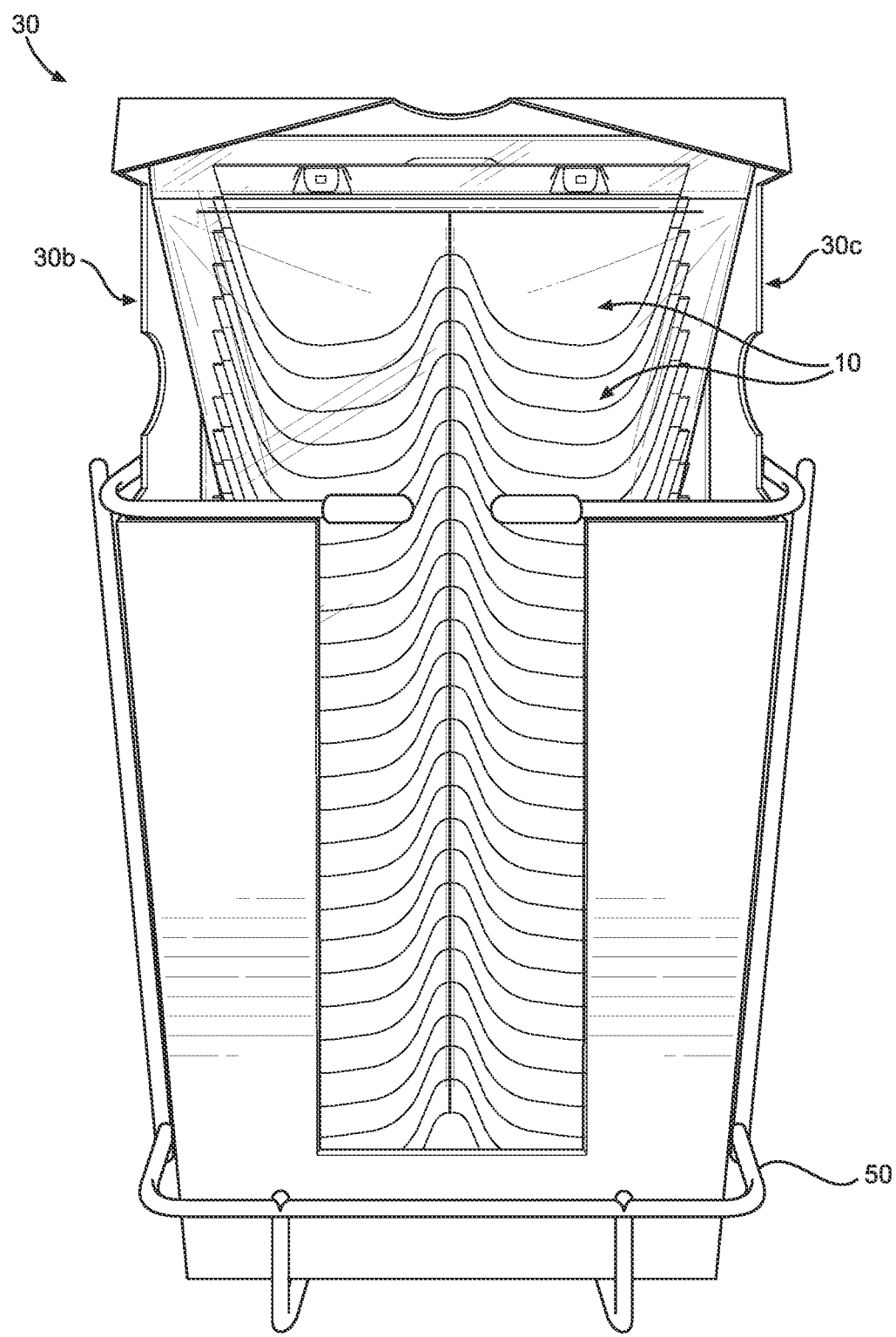
FIG. 26 shows the container configured for dispensing of the eye shields.

With reference now to FIGS. 24-26, there is shown a dispensing container 30 for the stacked eye shields 10. The dispensing container 30 is desirably configured for storing and shipment of the eye shields 10 in a stacked configuration as shown in FIG. 24, and for dispensing of the eye shields 10 to users of the eye shields, as shown in FIG. 26. The dispensing container 30 is also configured to be aesthetically pleasing and includes various ornamental aspects and features. The container 30 is also configured to facilitate the stacked eye shields and the dispensing of the of the eye shields in a manner such that a user can just grasp the top most eye shield 10 from the stack to remove it from the stack and not have to handle underlying ones.

The erected container includes a front 30a, sides 30b and 30c, rear 30d, bottom 30e, and top 30f. The front 30a, sides 30b and 30c, and rear 30d are vertical surfaces perpendicular to the bottom 30e and rise upwardly from bottom 30e, which is horizontal. The top 30f is slopes downwardly from the front 30a to the rear 30d and is disposed at an angle b relative to horizontal of from about 10 to about 35 degrees, most preferably between about 20-25 degrees.

As shown in FIGS. 21A-21D and 24, the eye shields 10 are substantially aligned to be substantially parallel to one another in the stack and are stacked in a sloped configuration in which the ear pieces 14 are generally aligned with one another and disposed at an angle c relative to the horizontal bottom 30e of from about 10 to about 35 degrees, most preferably between about 20 and 25 degrees. Thus, the top 30f is desirably sloped to be substantially parallel to the generally uniformly sloped ear pieces 14 of the stacked eye shields 10. It has been observed that the stacking features of the eye shields 10 tend to prevent at least the bulk of the eye shields from shifting and becoming entangled in the stack. That is, while a minor few of the eye shields could potentially shift a little from the stacked orientation as shown, it has been observed that the bulk of the eye shields do not shift and the stack does not become entangled such that a user can just grasp the top most eye shield from the stack to remove it from the stack and not have to handle underlying ones.

Figure 27:
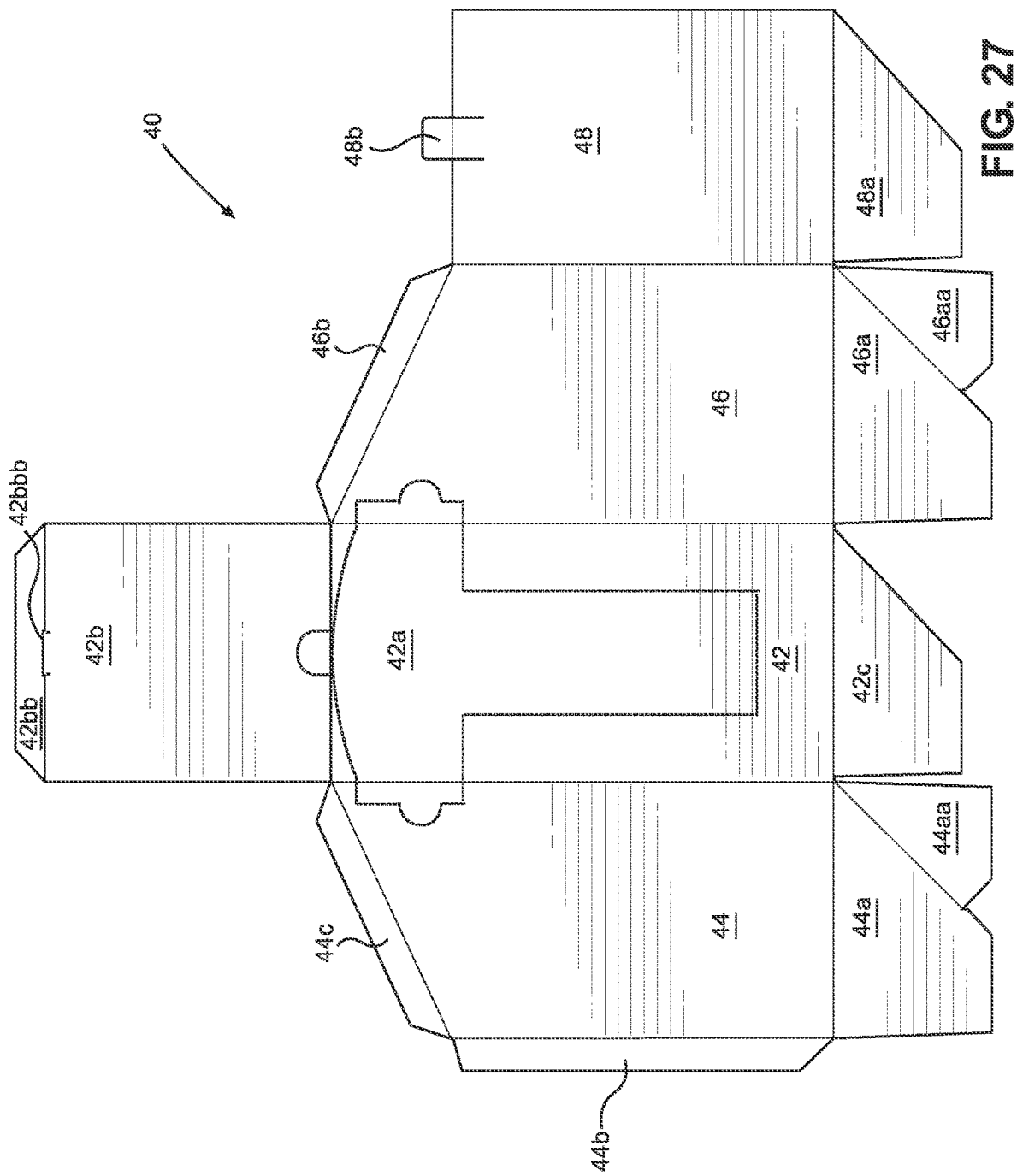
FIG. 27 shows a blank for making the container.
Figure 1:
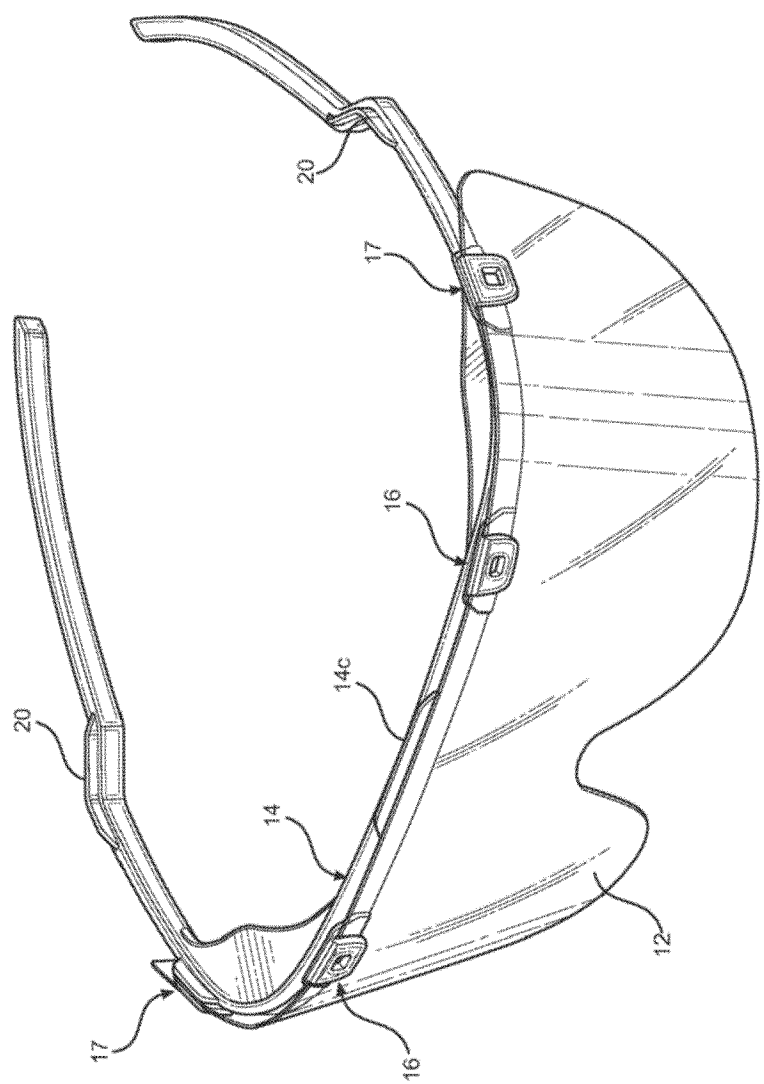
Figure 2:
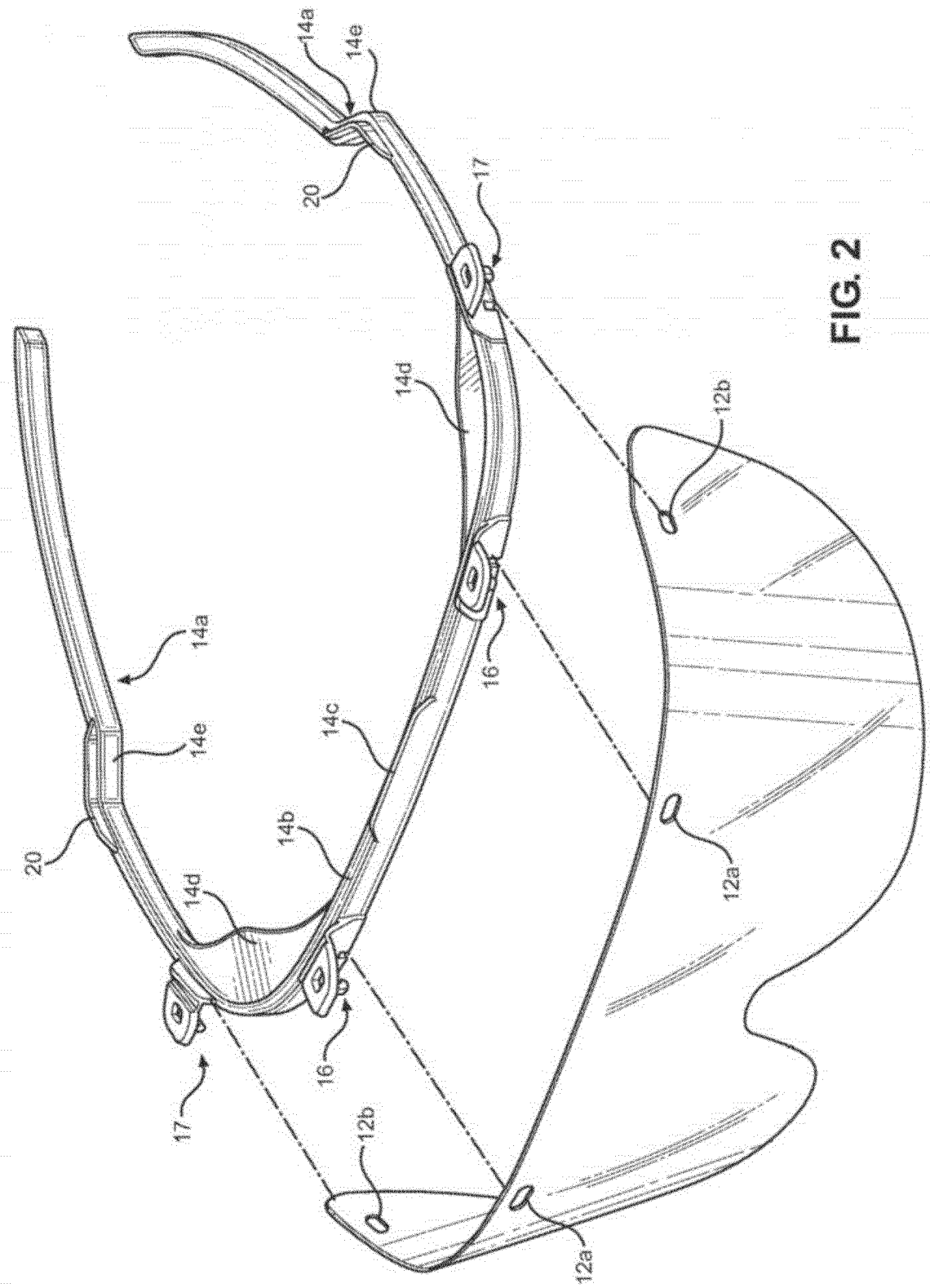
Figure 3:
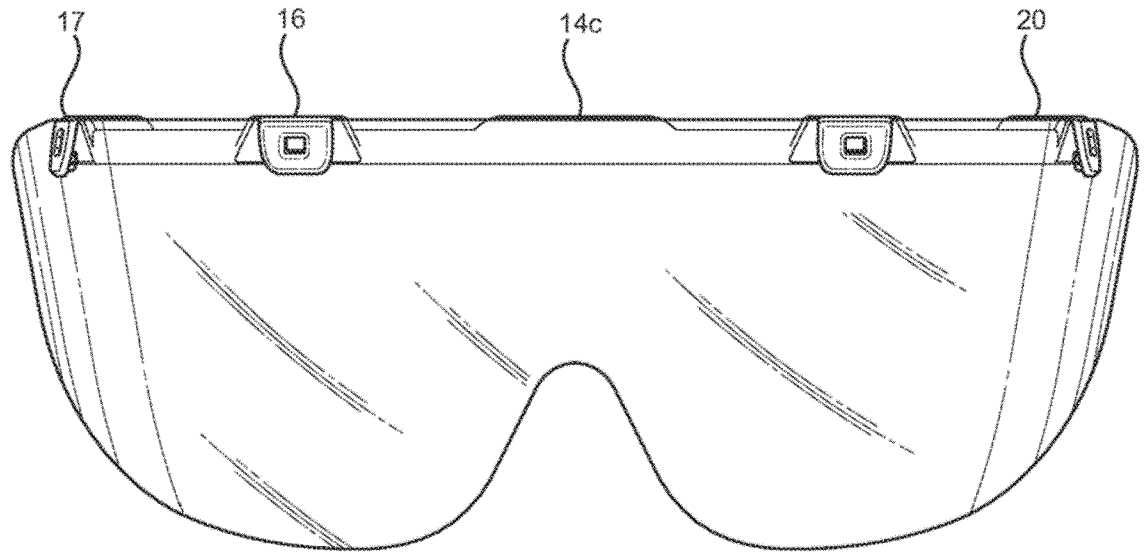
Figure 4:
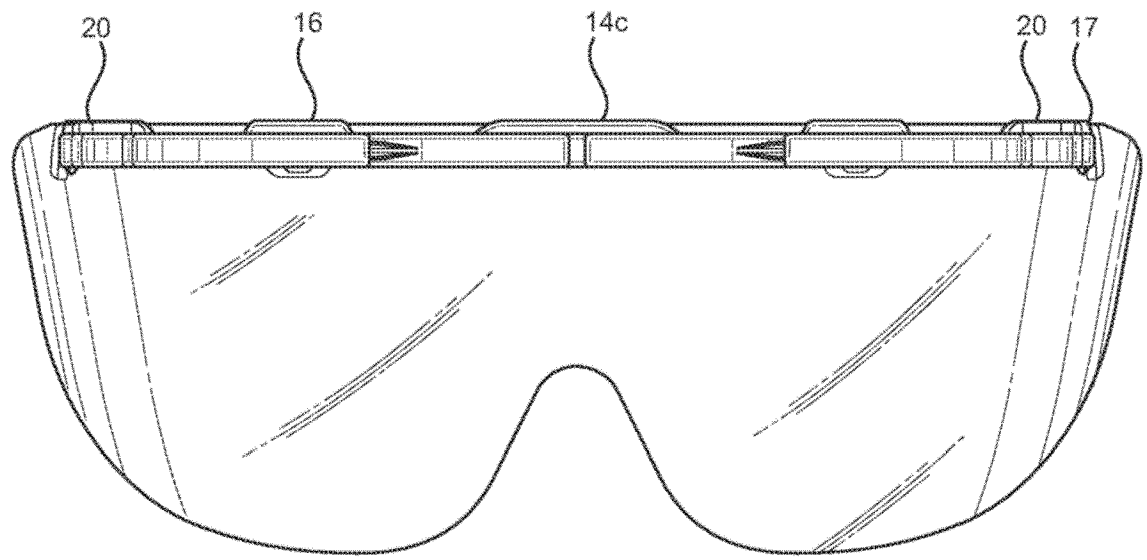
Figure 5:
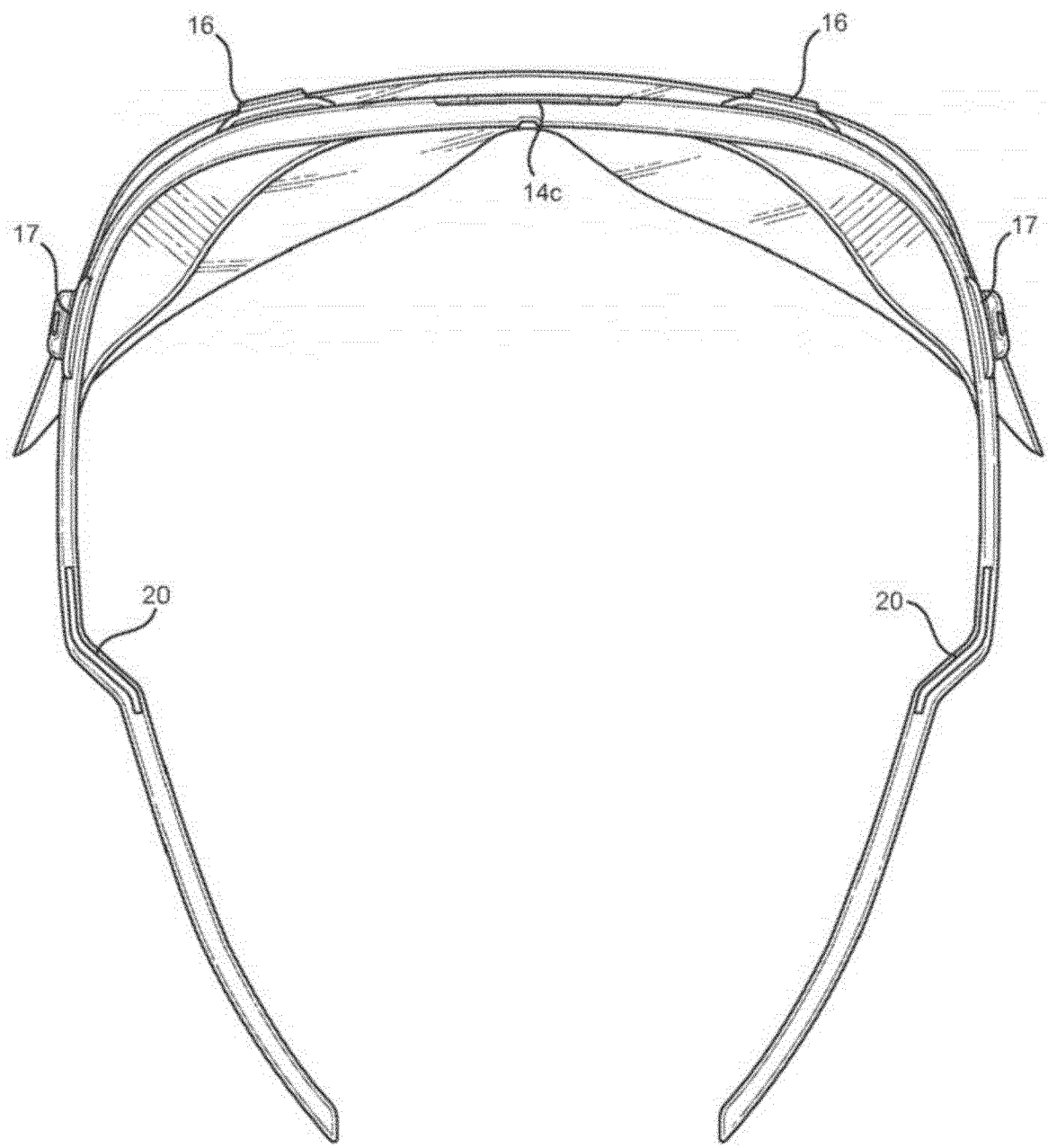
Figure 6:
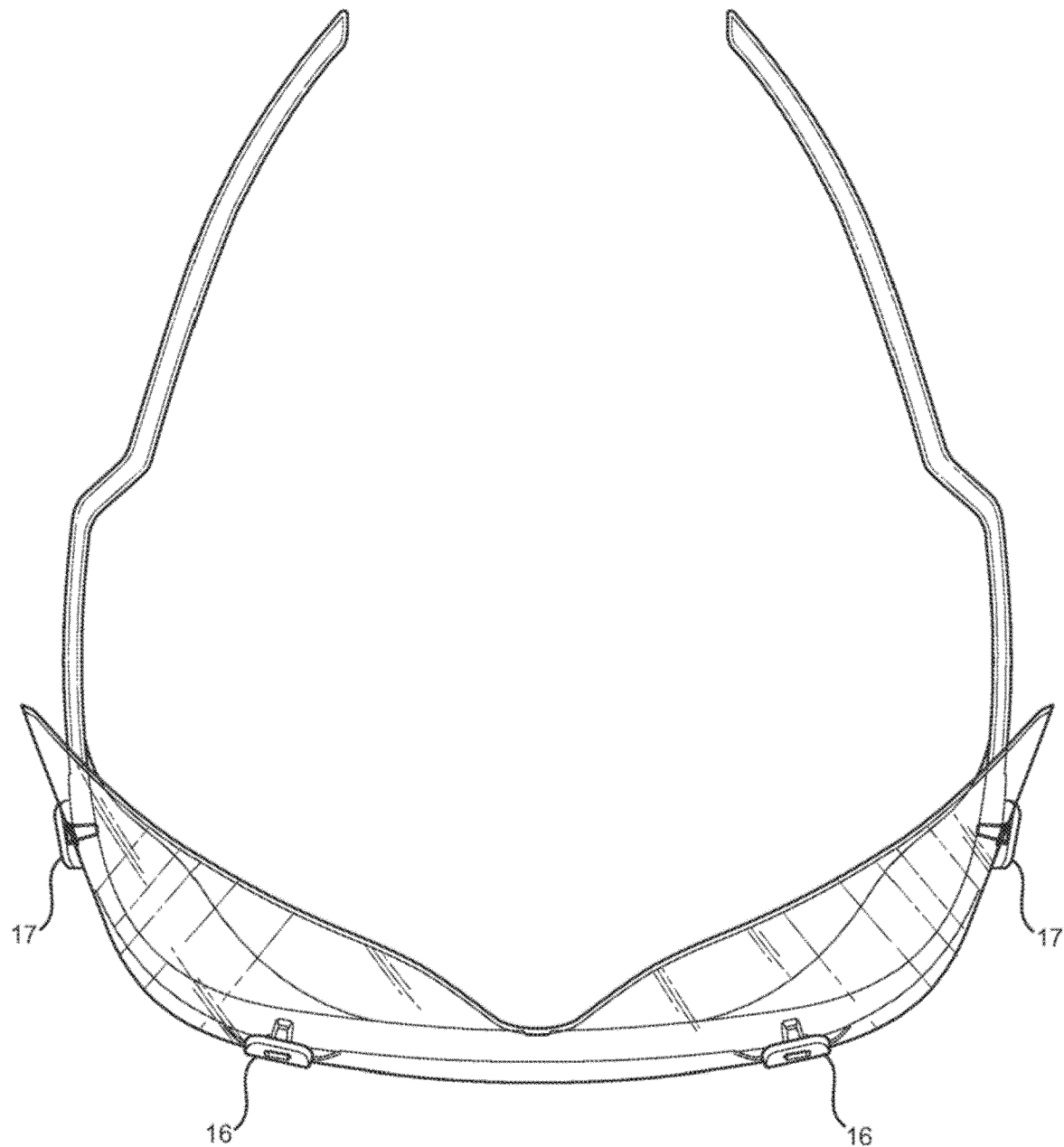
Figure 7:
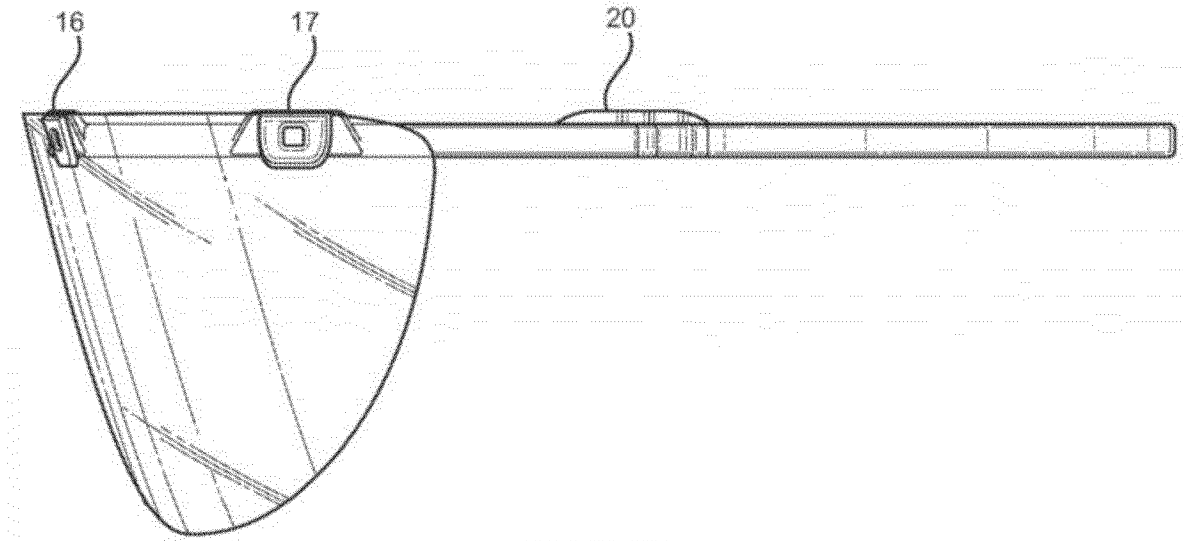
Figure 8:
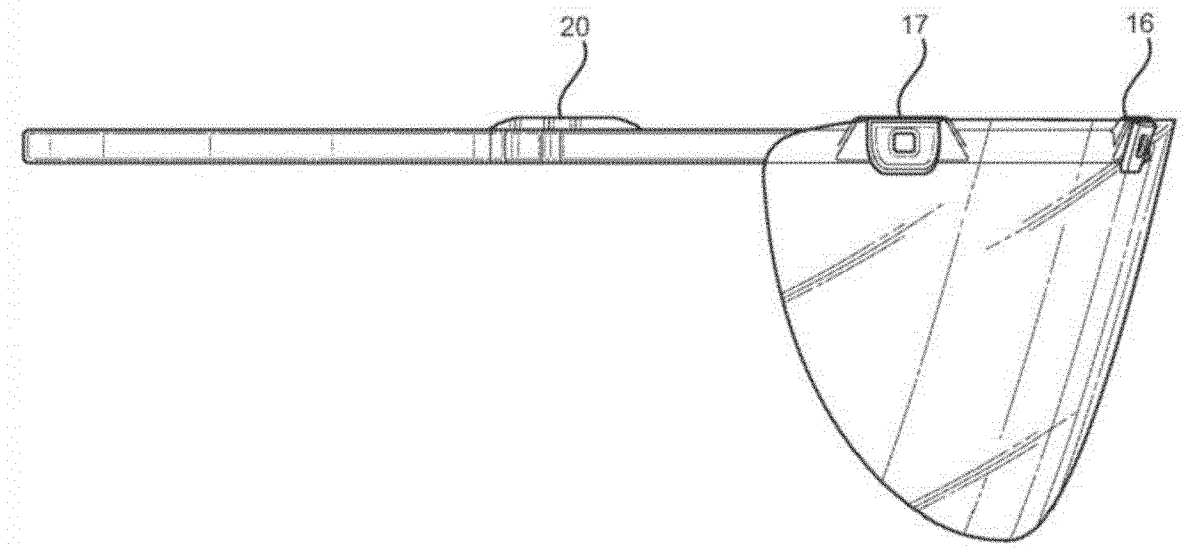
Figure 9:
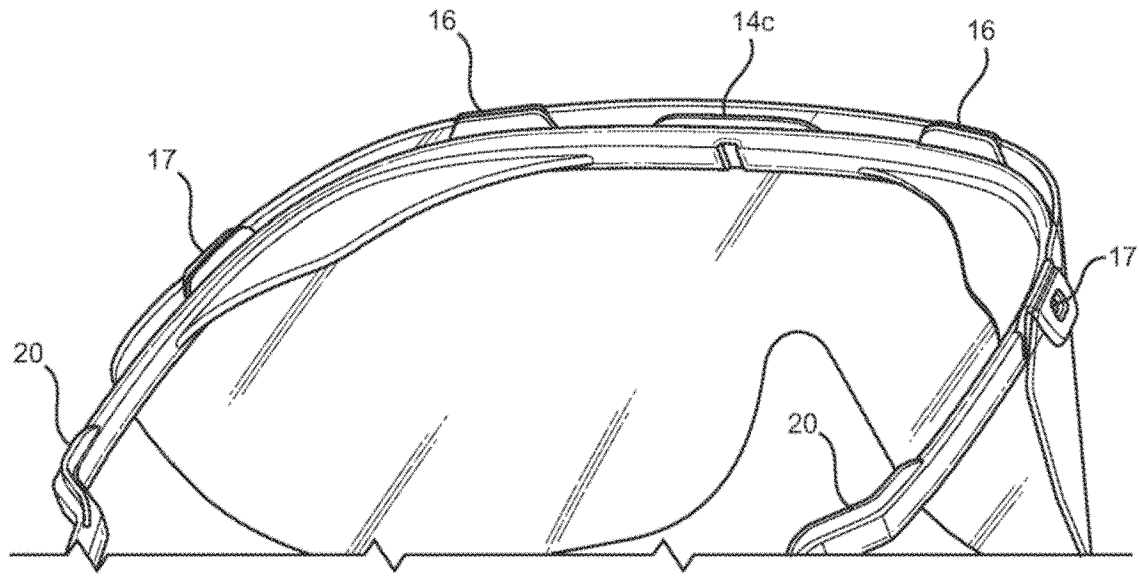
Figure 10:
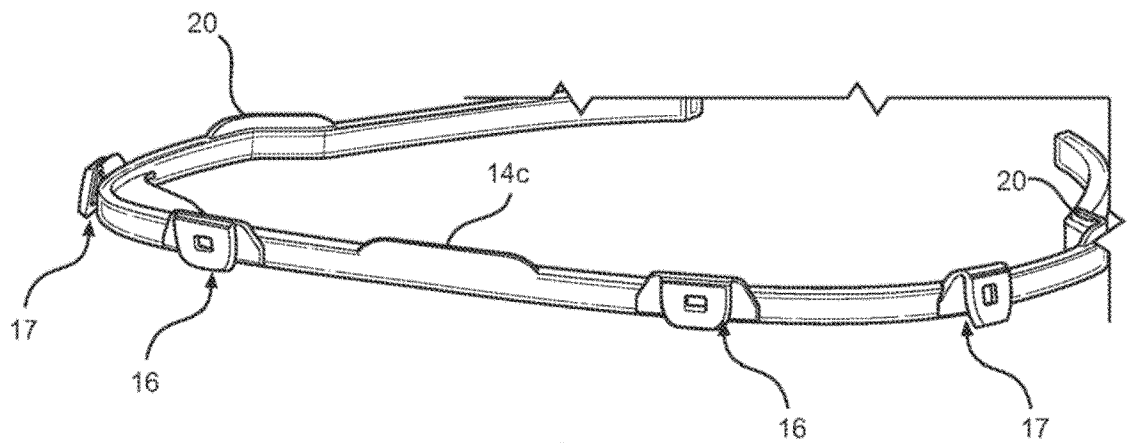
Figure 11:
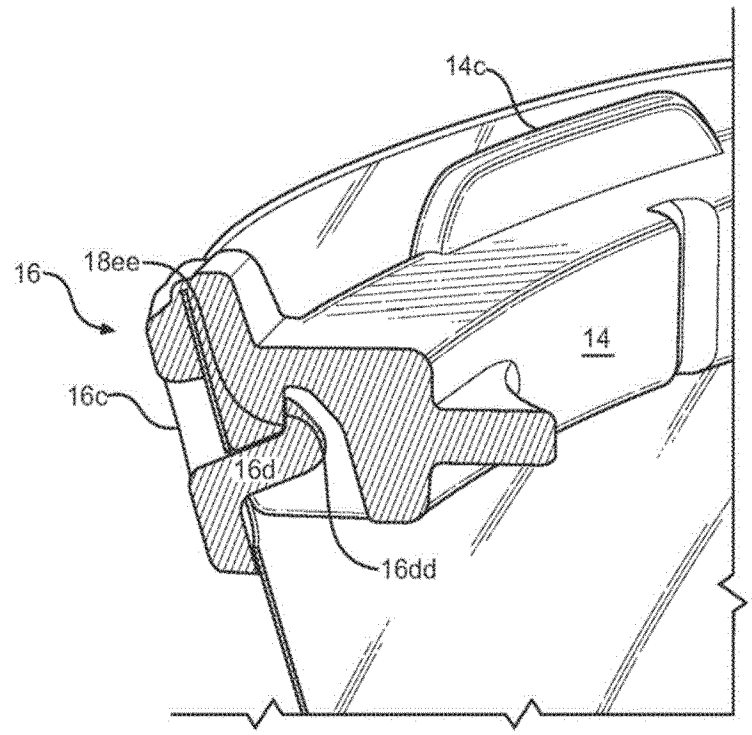
Figure 12:
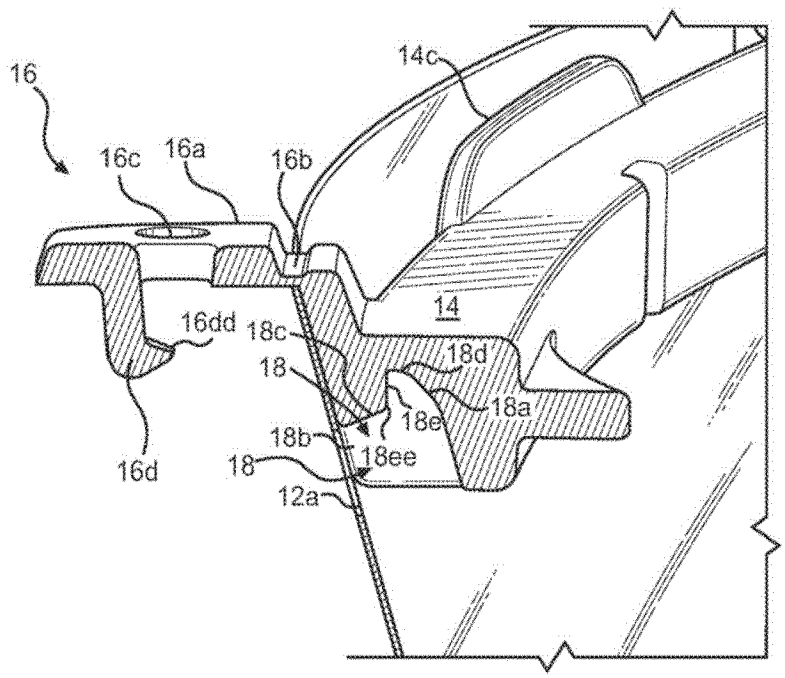
Figure 13:
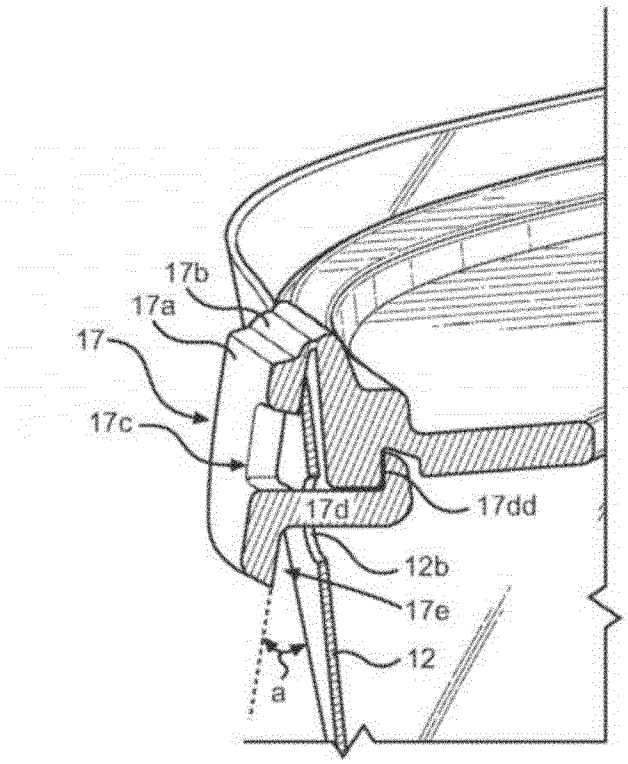
Figure 14:
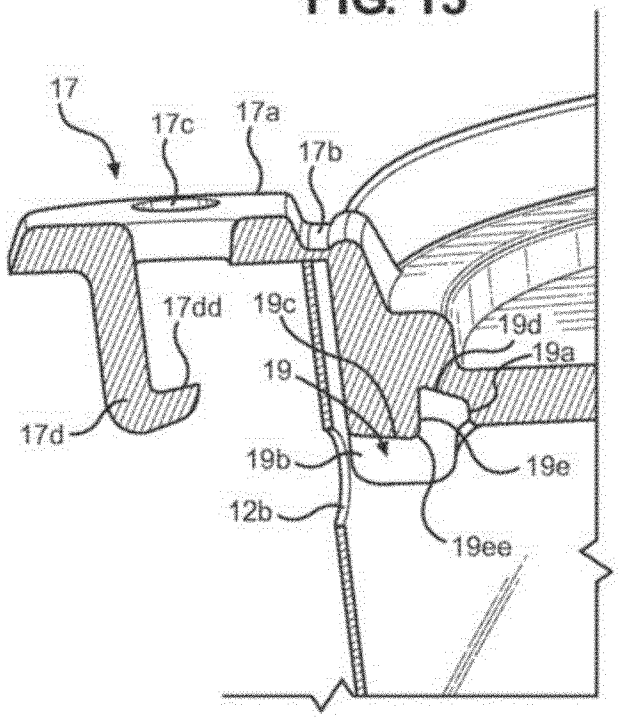
Figure 15:
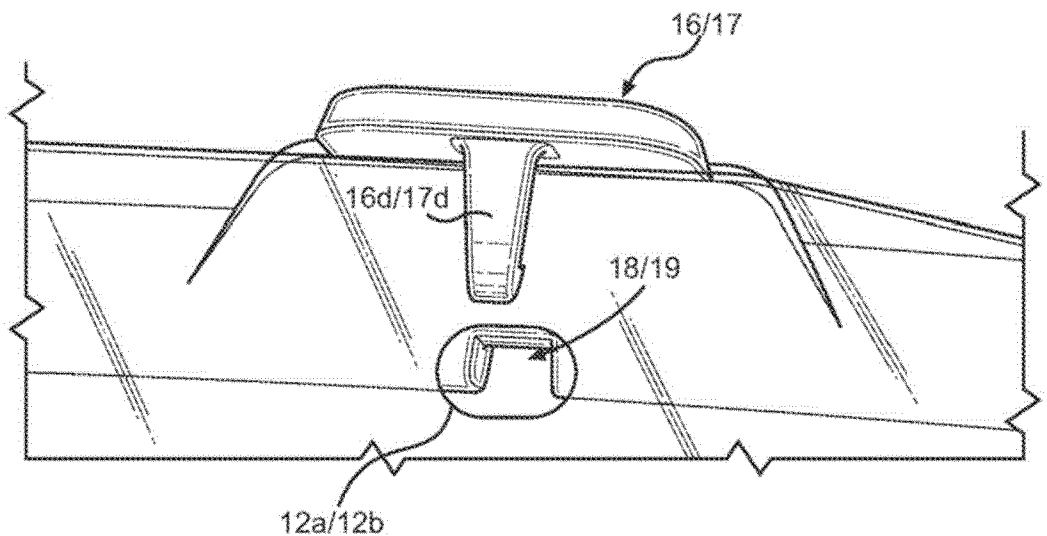
Figure 16:
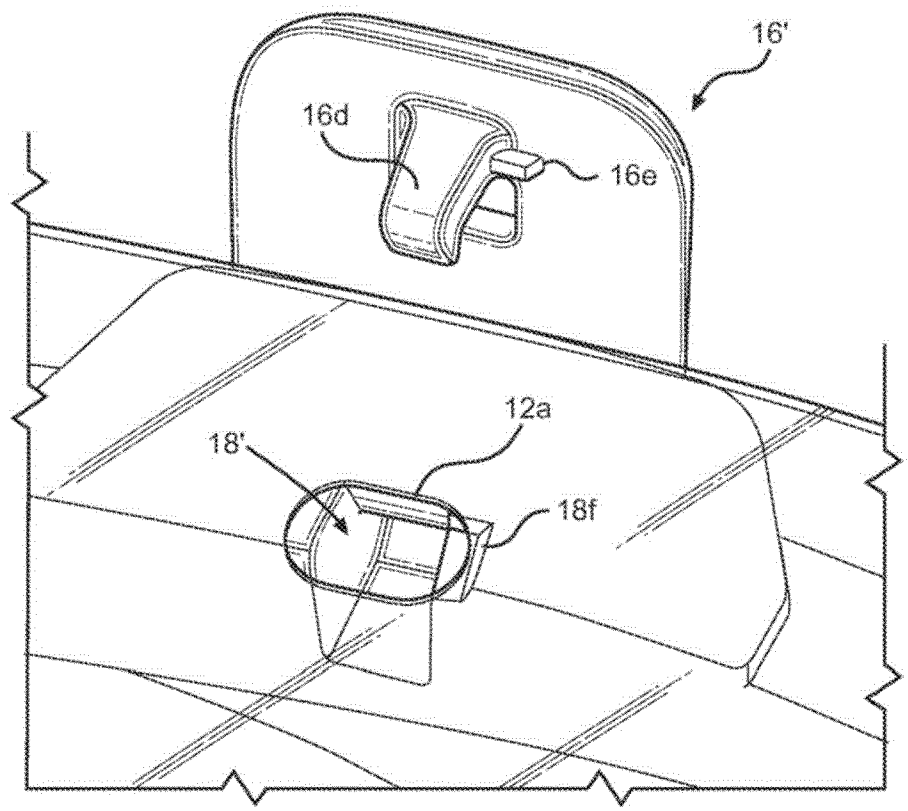
Figure 17:
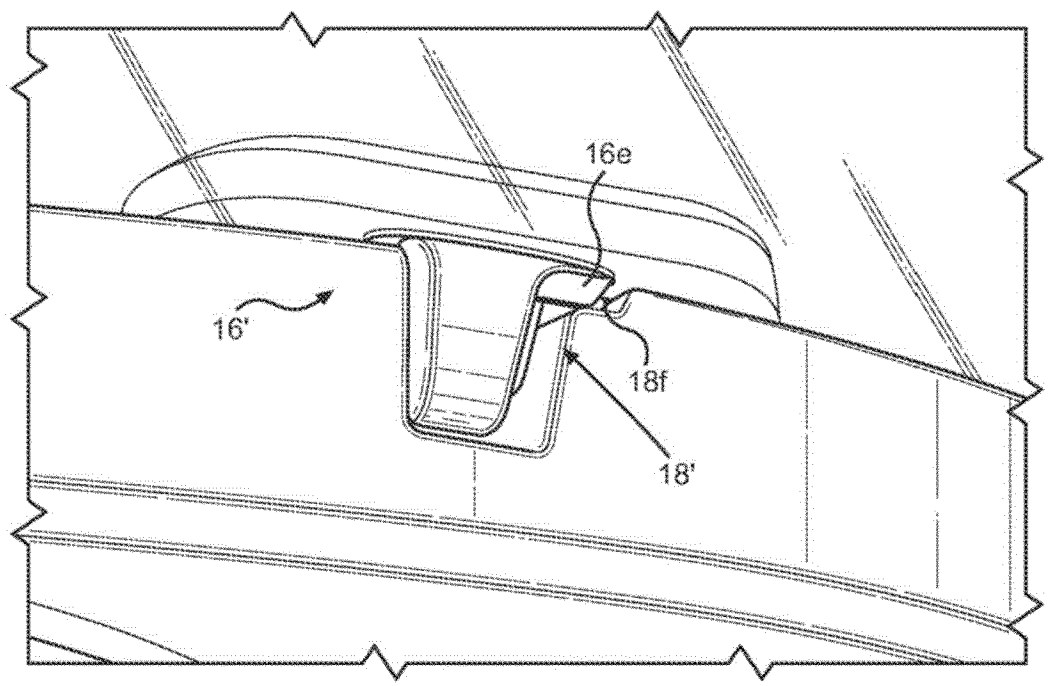
Figure 18:
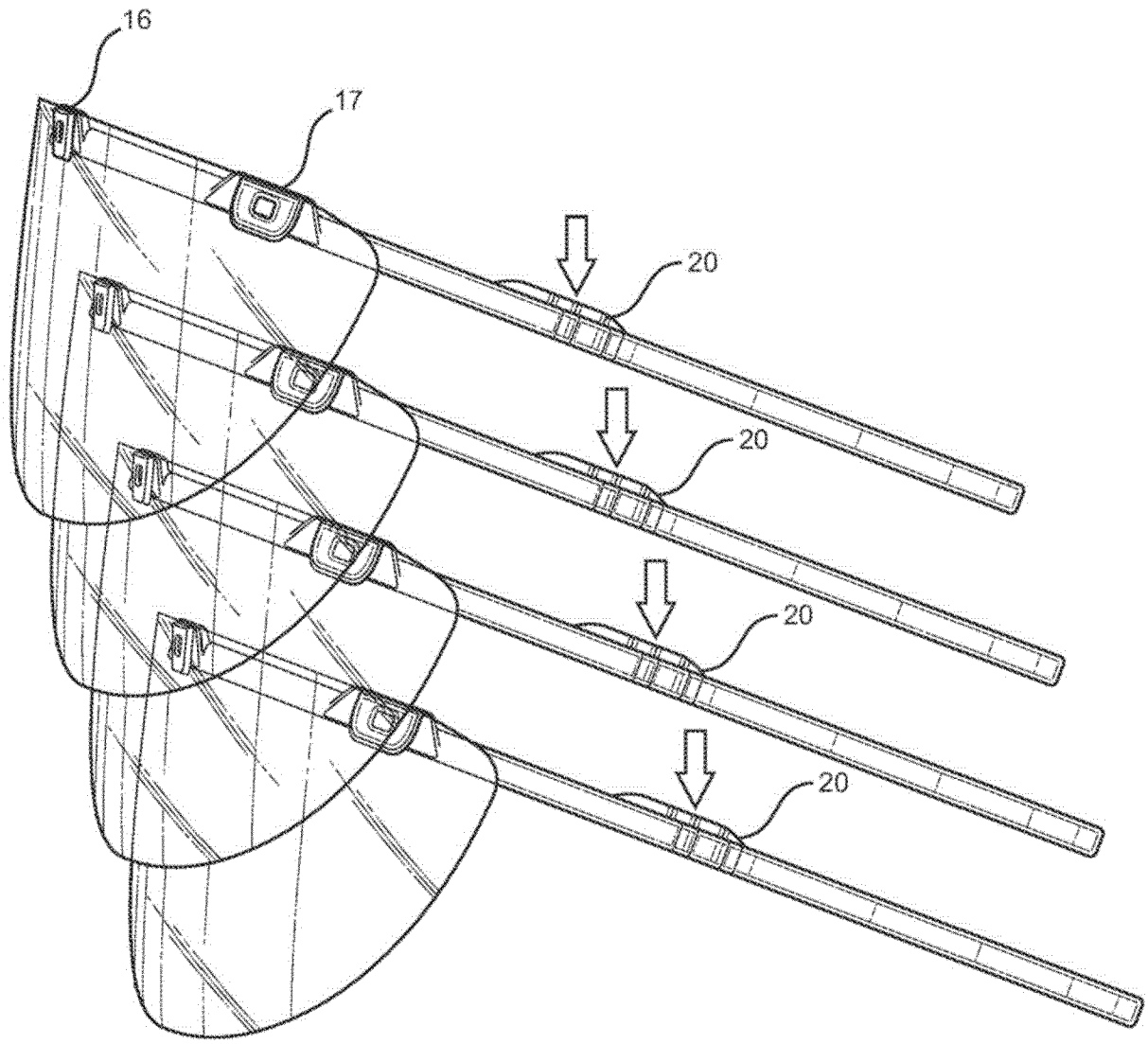
Figure 19:
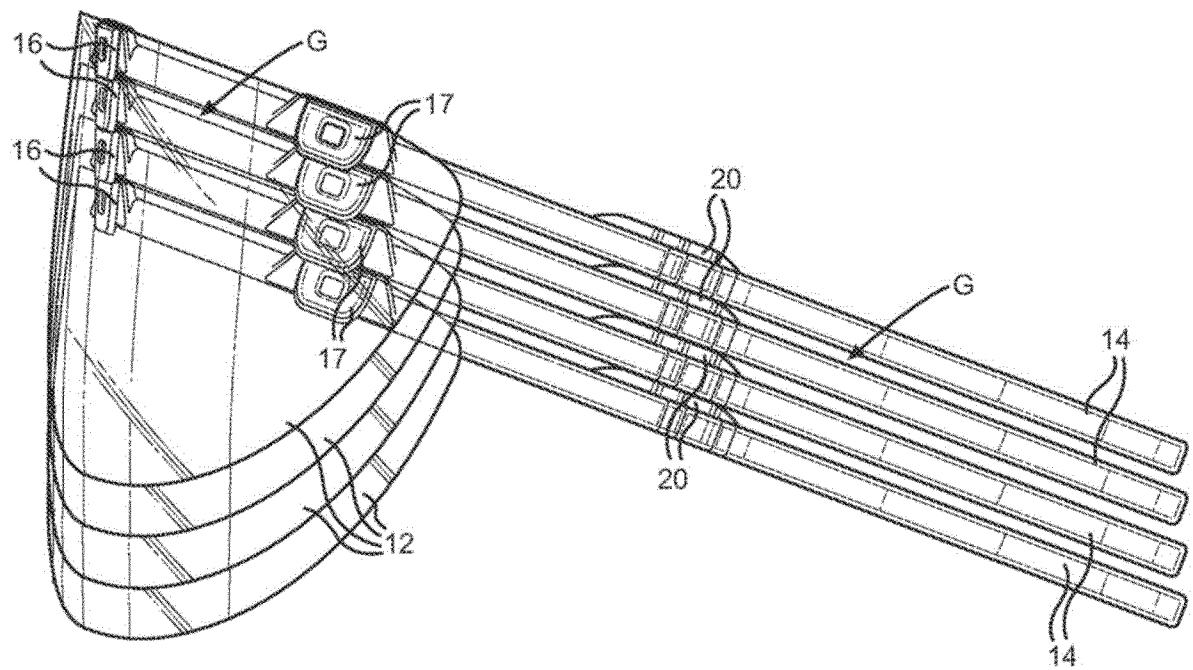
Figure 20:
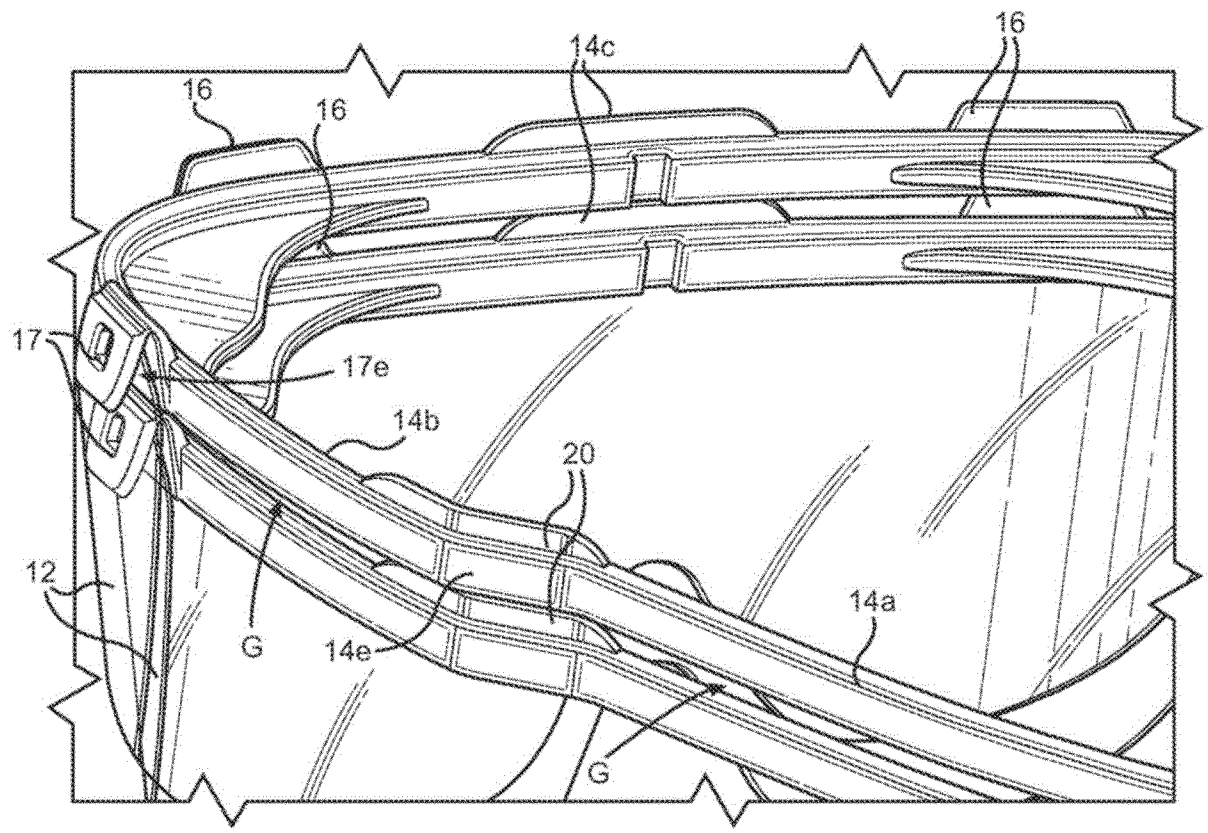
Figure 21A:
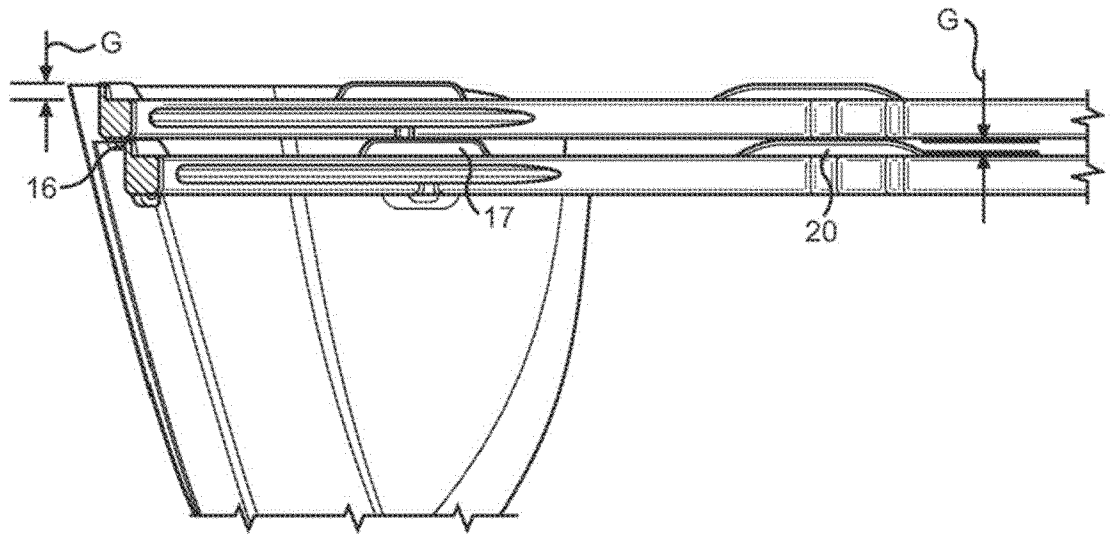
Figure 21B:
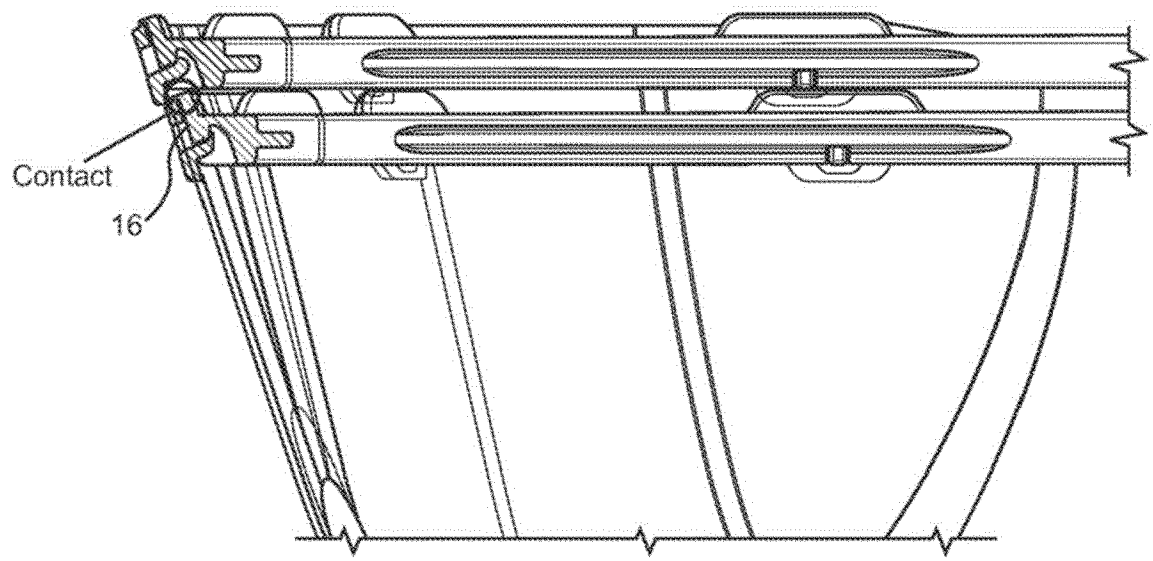
Figure 21C:
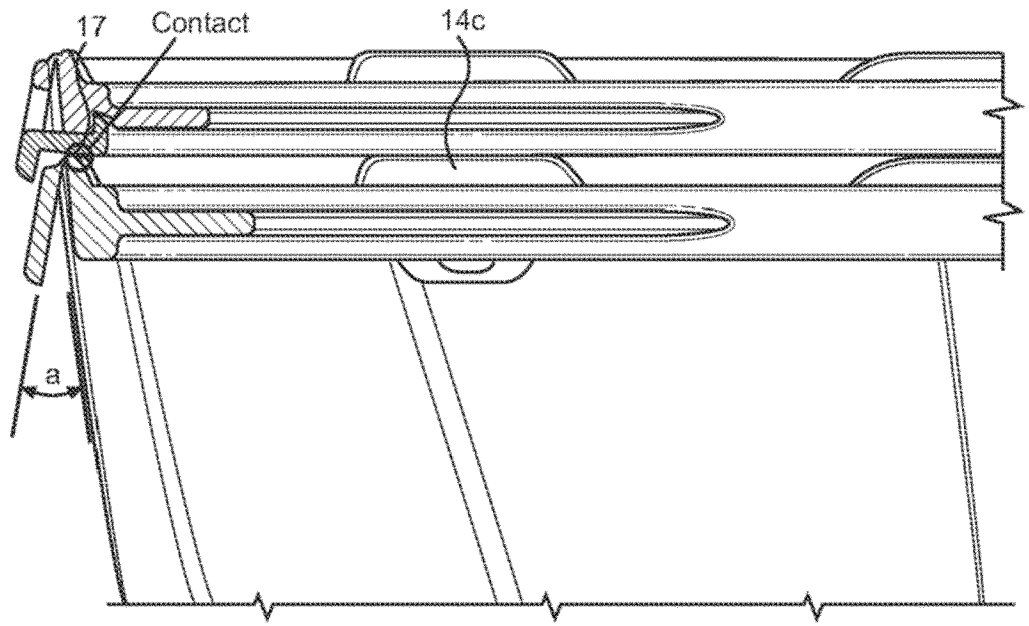
Figure 21D:
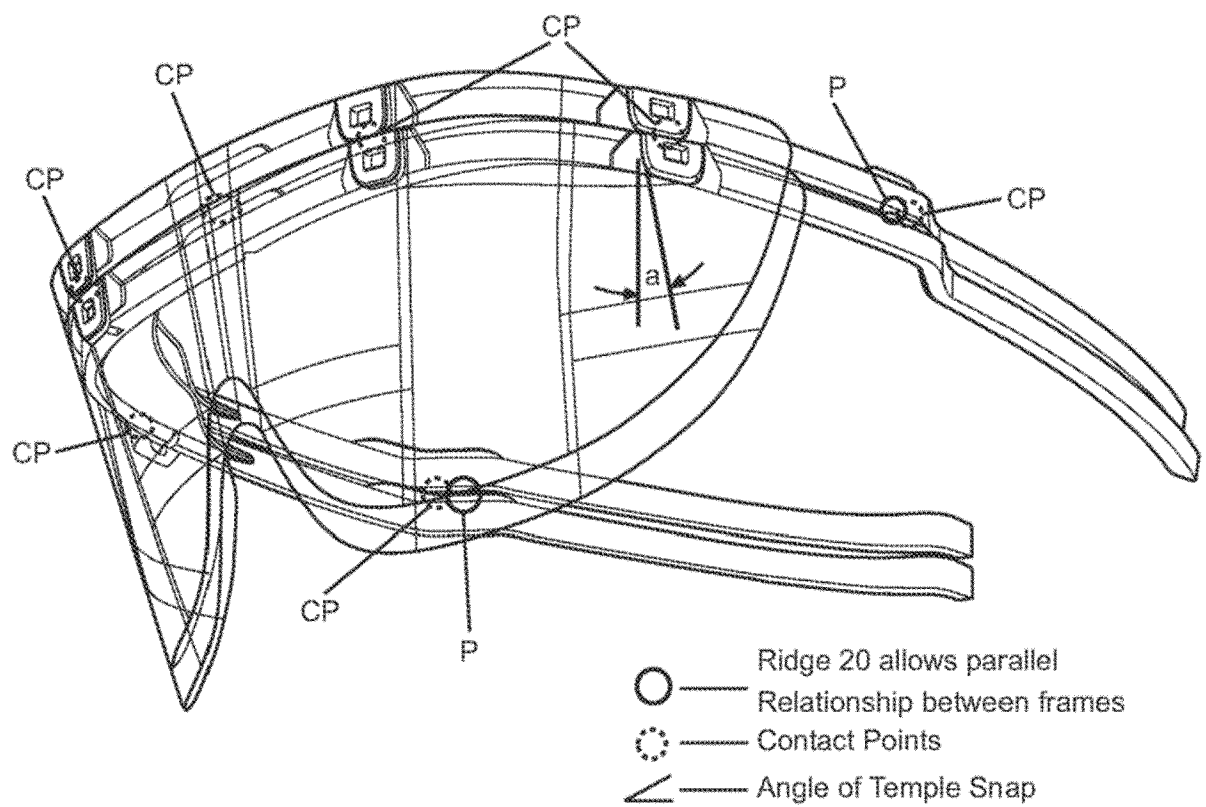
Figure 22:
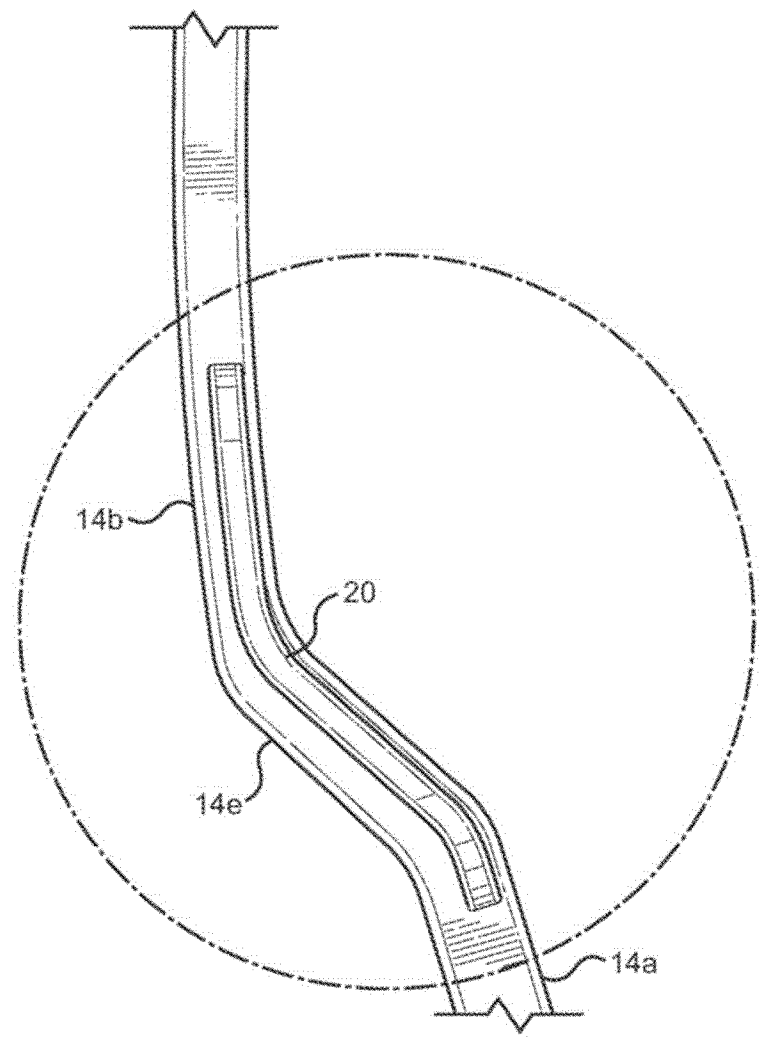
Figure 23:
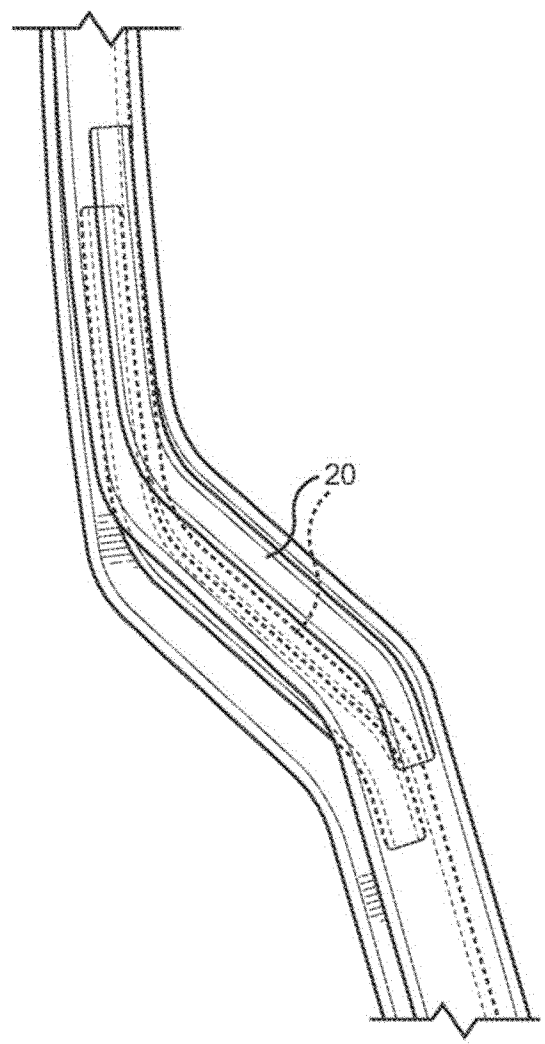
Figure 24:
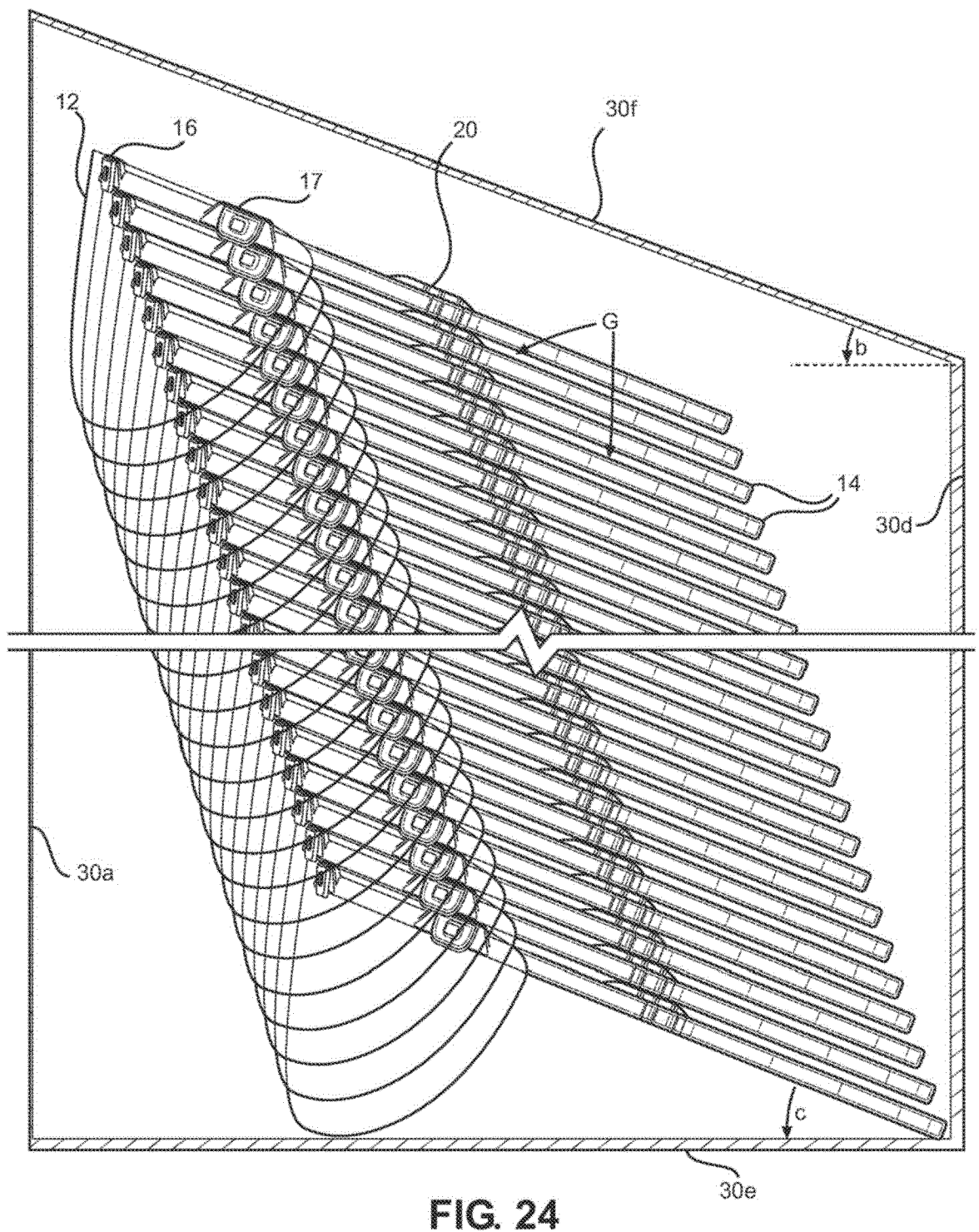
Figure 25:
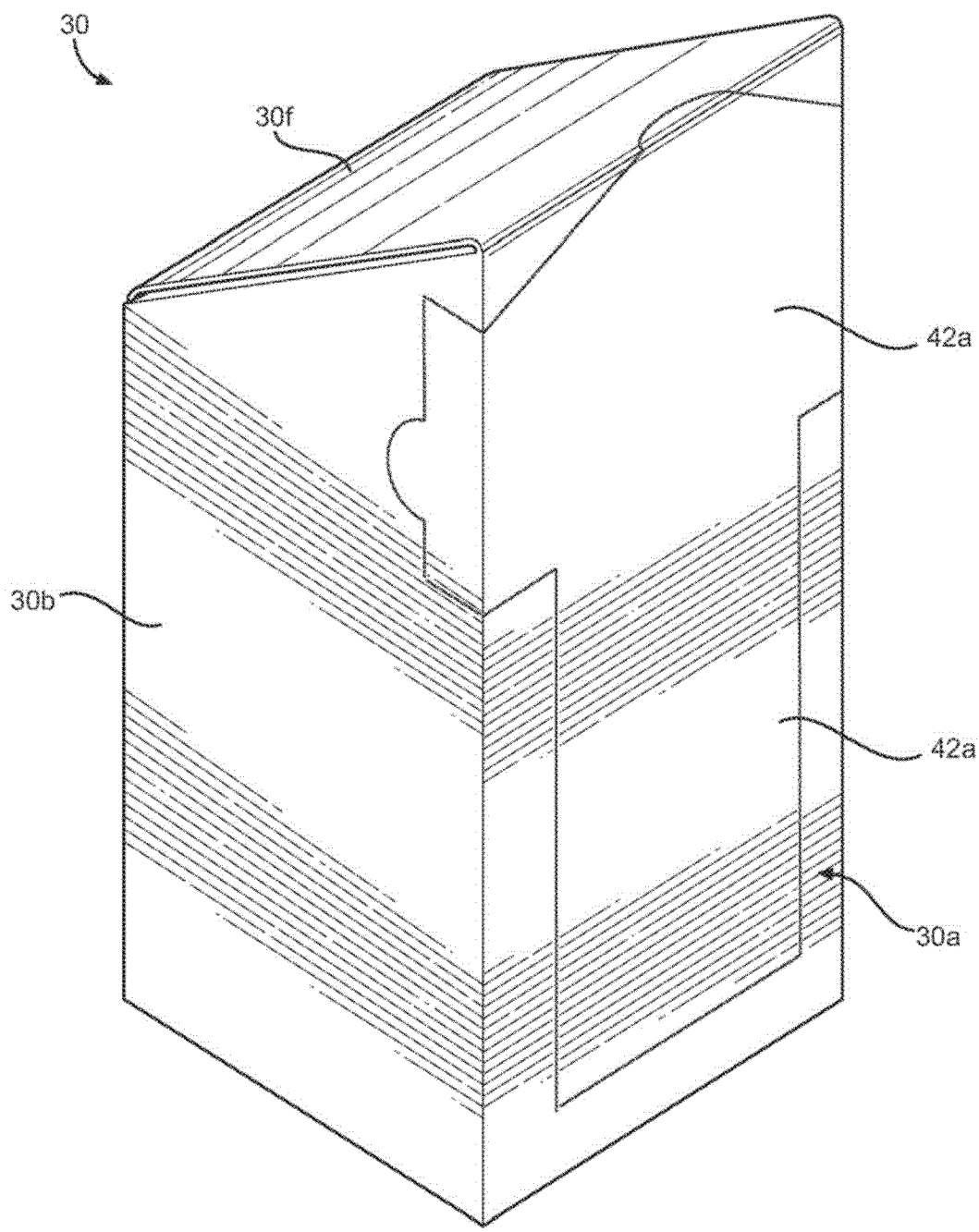
Figure 26:
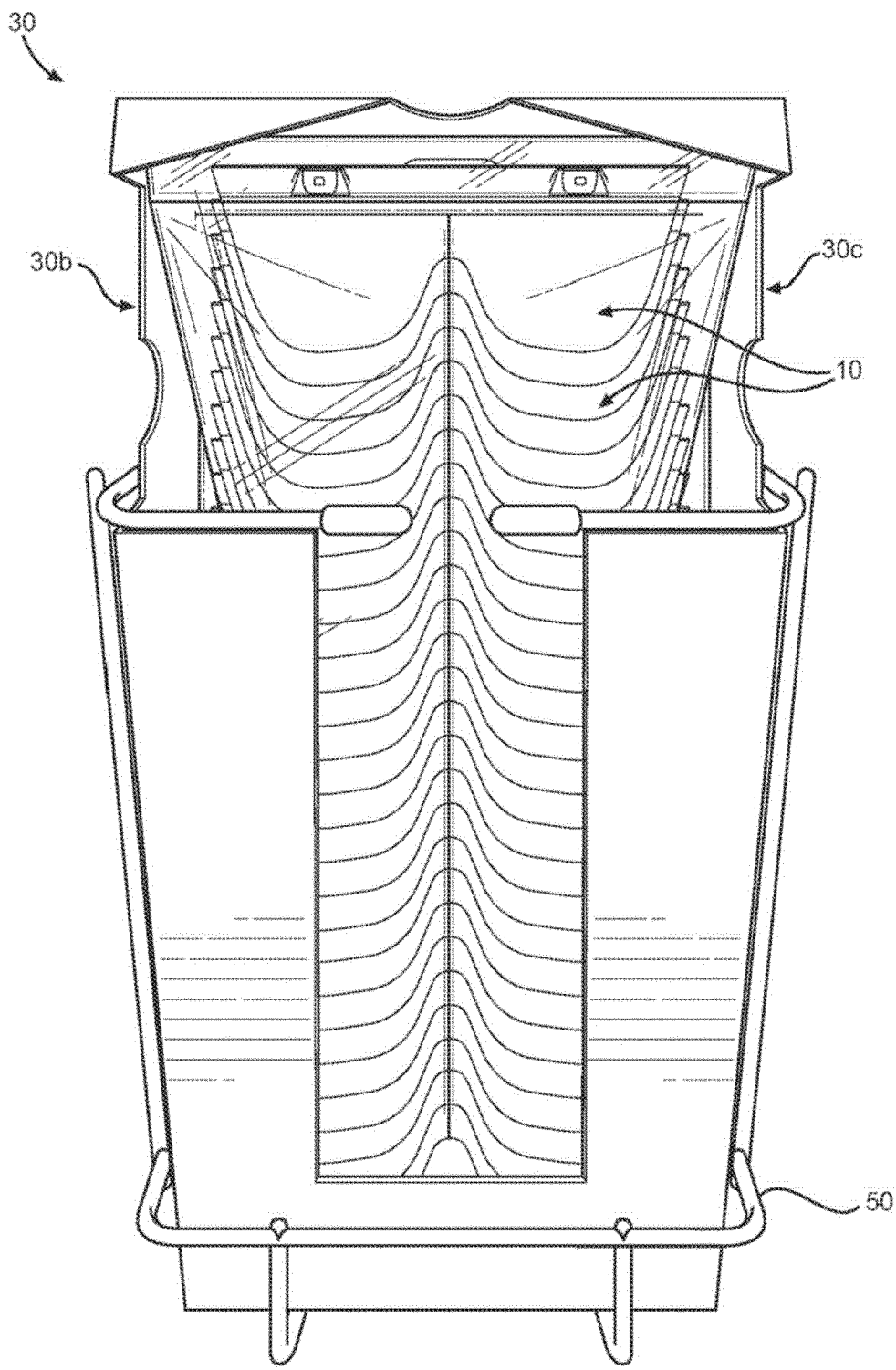

The dispensing container 30 may be of paperboard construction and formed of a one-piece blank 40, as shown in FIG. 27. The dispensing container 30 may be hung from a wall or the like, and may be supported by a wire hanger 50 that can be attached to a wall (FIG. 26).

Returning to FIG. 27, the blank 40 includes a front panel 42, opposite side panels 44 and 46 foldable relative to the front panel 42, and rear panel 48 foldable relative to the side panel 46.

The front panel 42 includes a tear-away section 42a having a border formed by perforations and configured to be removed to enable access to the stacked eye shields 10, a foldable top flap 42b, and a folding edge 42bb extending from the top flap 42b, with a slot 42bbb formed along the edge 42bb. The tear-away section 42 is generally T-shaped and includes portions that extend into the top flap 42b and the side panels 44 and 46 to facilitate access of the fingers of a user into the container 30 for removing the eye shields 10, generally one at a time, from the stack of eye shields in the container 30.

The side panel 44 includes a bottom flap 44a having a folding edge 44aa, a side flap 44b, and an upper flap 44c. The side panel 46 includes a bottom flap 46a having a folding edge 46aa, and an upper flap 46b. The rear panel 48 is includes a bottom flap 48a and an upper folding tab 48b configured to engage the slot 42bbb.

As will be appreciated, the disclosure advantageously provides eye shields configured to facilitate stacking of the eye shields so that the eye shields remain aligned and parallel to one another and do not entangle so that a user can just grasp the top most eye shield from the stack and not have to handle underlying ones.

The present disclosure advantageously also advantageously provides eye shields having a snap-fit feature that enables the lens to be easily attached to the frame and also to be easily removed for cleaning or replacement. The snap-fit feature is also specially configured to facilitate stacking of the eye shields.

A container that compliments the stacked eye shields is also provided which facilitates shipping and dispensing of the eye shields.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

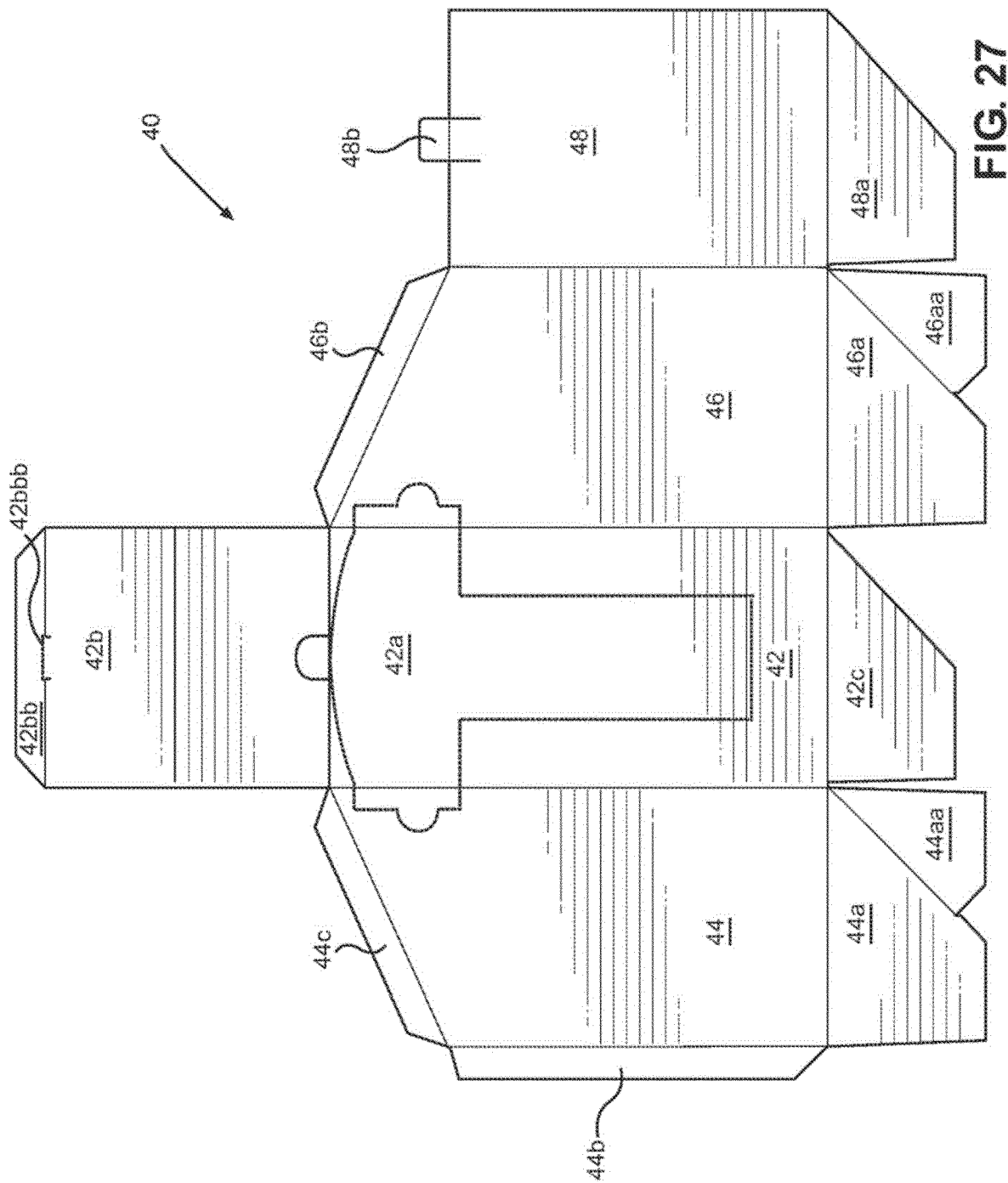

The invention claimed is:

1. A stack of eye shields, comprising
   a plurality of eye shields, each eye shield having:
   a frame having at least two receivers located along the frame and at least two latches, each of the latches located to engage one of the receivers, one of the latches including an outwardly extending rib, and one of the receivers including a pocket configured to snugly receive the rib, the frame having a plurality of spaced apart elevated support surfaces along and rising above an upper portion of the frame; and
   a lens installed on the frame and having at least two lens apertures extending through the lens, each of the apertures aligned with one of the receivers of the frame with each of the latches engaged with one of the receivers securing the lens to the frame, the rib and the pocket cooperating to inhibit the lens from shifting side-to-side;
   wherein the plurality of eye shields is provided in a stack with the eye shields stacked one on top of another with each of the eye shields and lenses oriented substantially vertical and parallel to one another one of the eye shields with each of the elevated surfaces of an overlying one of the frames of the eye shields in the stack being slightly forward of and overlapping a corresponding one of the elevated surfaces of an immediately underlying one of the frames of the eye shields in the stack, with each frame of each eye shield of the stack having a gap therebetween except at contact surfaces of the frames where the elevated support surfaces contact an adjacent lower surface of the frame of its overlying eye shield, whereby the elevated support surfaces of the frames stabilize the stack of the eye shields for shipping and dispensing of the stack of the eye shields.

2. The stack of eye shields of claim 1, wherein the elevated support surfaces comprise elongate, narrow ridges that define crooked raised lines along upper portions of the frame.

3. The stack of eye shields of claim 2, wherein the elevated support surfaces further comprise uppermost surfaces of the latches elevated above the frame that lie in a common plane with the elongate, narrow ridges.

4. The stack of eye shields of claim 2, wherein the elevated support surfaces further comprise a stiffener elevated above the frame that lies in a common plane with the elongate narrow ridges.

5. The stack of eye shields of claim 1, wherein the elevated support surfaces are located at temple locations of the frame.

6. The stack of eye shields of claim 1, wherein the latches include a lowermost rear surface angled away from the lens to provide a pocket that provides clearance for the lens of the underlying eye shield in the stack.

7. The stack of eye shields of claim 1, wherein the stack is in a sloped configuration in which ear pieces of the frames of the eye shields are generally aligned with one another and disposed at an angle relative to horizontal bottom of from about 10 to about 35 degrees.

8. The stack of eye shields of claim 7, further comprising a container into which the stack of eye shields is received for shipping and dispensing, the container having a top sloped to be substantially parallel to the ear pieces of the stack of eye shields.

9. The stack of eye shields of claim 1, wherein each of the receivers comprises an elongate cavity having an open front with a sloped entrance wall extending upwardly from the open front at an angle, and a catch wall located behind the sloped entrance wall, the catch wall defining a catch surface, and each of the latches comprises a flap hingedly connected to the frame, and a void area formed on the flap configured to impart flexion to the flap when pressure is applied to a lower edge of the flap, an elongate catch extending upwardly at an angle from an inner surface of the flap corresponding substantially to the angle of the sloped entrance wall, and a tooth projecting from a distal end of the elongate catch and configured to engaging the catch surface of the catch wall.

* * * * *

UNITED STATES PATENT AND TRADEMARK OFFICE
CERTIFICATE OF CORRECTION

PATENT NO. : 11,911,317 B2
APPLICATION NO. : 17/477697
DATED : February 27, 2024
INVENTOR(S) : Walter C. Cowart et al.

Page 1 of 23

It is certified that error appears in the above-identified patent and that said Letters Patent is hereby corrected as shown below:

On the Title Page

Place replace the illustrative figure, FIG. 27, with the corrected FIG. 27, as shown on the attached drawing sheet 22 of 22.

In the Drawings

Replace drawing sheets 1-22, as shown on the attached pages.

Signed and Sealed this
Third Day of June, 2025

Coke Morgan Stewart
*Acting Director of the United States Patent and Trademark Office*